US010286161B2

(12) United States Patent
 Persons

(10) Patent No.: US 10,286,161 B2
(45) Date of Patent: May 14, 2019

(54) INTEGRATED NEEDLE AND CANNULA FOR PLASTIC SURGERY

(71) Applicant: Barbara Persons, Lafayette, CA (US)

(72) Inventor: Barbara Persons, Lafayette, CA (US)

( * ) Notice: Subject to any disclaimer, the term of this patent is extended or adjusted under 35 U.S.C. 154(b) by 99 days.

(21) Appl. No.: 15/242,455

(22) Filed: Aug. 19, 2016

(65) Prior Publication Data
US 2017/0049972 A1    Feb. 23, 2017

Related U.S. Application Data

(60) Provisional application No. 62/207,886, filed on Aug. 20, 2015.

(51) Int. Cl.
*A61M 5/32* (2006.01)
*A61B 17/06* (2006.01)
(Continued)

(52) U.S. Cl.
CPC ..... *A61M 5/3297* (2013.01); *A61B 17/06066* (2013.01); *A61M 5/178* (2013.01);
(Continued)

(58) Field of Classification Search
CPC .............. A61B 17/06066; A61B 17/34; A61B 17/3468; A61B 2017/00792;
(Continued)

(56) References Cited

U.S. PATENT DOCUMENTS 4,772,264 A    9/1988 Cragg
4,828,547 A    5/1989 Sahi et al.
(Continued)

OTHER PUBLICATIONS

International Search Report from PCT/US16/47917, dated Jan. 17, 2017 (5 sheets).

*Primary Examiner* — Imani N Hayman
(74) *Attorney, Agent, or Firm* — Sideman & Bancroft LLP; Guy W. Chambers

(57) ABSTRACT

An integrated needle and cannula assembly for plastic surgery including a syringe connected to a blunt-tipped cannula where the blunt-tipped cannula is inserted into the hollow annular space of a hypodermic needle. In operation, the medical practitioner penetrates into the patient's skin using the hypodermic needle and then slides the blunt-tipped cannula through the annular space of the needle. A transporter assembly can be interposed between the syringe and the overlapping needle/cannula. The transporter assembly may include a retractable inner needle tube attached to the hypodermic needle and an external transporter housing which connects the syringe to the cannula through a cannula connector. Once the blunt tipped cannula is under the patient's skin, the needle is preferably withdrawn from the patient's skin to allow sub-dermal substances to be injected using only the blunt-tipped cannula. Withdrawal of the needle can be assisted with either a pull spring or push spring. In an alternative embodiment, a sharp-tipped trocar inside a cannula is used to penetrate the patient's skin. In a further alternative embodiment, a barbed surgical thread may be attached to said cannula to perform thread-lift procedures.

17 Claims, 25 Drawing Sheets

(51) Int. Cl.
*A61M 19/00* (2006.01)
*A61M 5/178* (2006.01)
*A61B 17/34* (2006.01)
*A61F 2/00* (2006.01)
*A61B 17/00* (2006.01)

(52) U.S. Cl.
CPC ........ *A61M 5/3232* (2013.01); *A61M 5/3286* (2013.01); *A61M 5/3287* (2013.01); *A61M 19/00* (2013.01); *A61B 17/34* (2013.01); *A61B 17/3468* (2013.01); *A61B 2017/00792* (2013.01); *A61B 2017/06009* (2013.01); *A61B 2017/06052* (2013.01); *A61B 2017/06085* (2013.01); *A61B 2017/06176* (2013.01); *A61F 2/0059* (2013.01); *A61M 2202/203* (2013.01); *A61M 2210/04* (2013.01)

(58) Field of Classification Search
CPC .......... A61B 2017/06009; A61B 2017/06052; A61B 2017/06085; A61B 2017/06176; A61F 2/0059; A61M 19/00; A61M 2202/203; A61M 2210/04; A61M 5/178; A61M 5/3232; A61M 5/3286; A61M 5/3287; A61M 5/3297
See application file for complete search history.

(56) References Cited

U.S. PATENT DOCUMENTS

| | | |
|---|---|---|
| 5,685,852 A | 11/1997 | Turkel et al. |
| 5,704,914 A | 6/1998 | Stocking et al. |
| 6,228,049 B1 | 5/2001 | Schroeder et al. |
| 6,391,007 B2 | 5/2002 | Chang et al. |
| 6,447,477 B2 | 9/2002 | Burney et al. |
| 6,936,006 B2 | 8/2005 | Sabre |
| 7,338,465 B2 | 3/2008 | Patton |
| 8,092,424 B2 | 1/2012 | Mueller et al. |
| 8,840,588 B2 | 9/2014 | Clement et al. |
| 9,414,930 B2 | 8/2016 | Lee |
| 2001/0025158 A1 | 9/2001 | Chang et al. |
| 2008/0281292 A1 | 11/2008 | Hickingbotham et al. |
| 2009/0069751 A1* | 3/2009 | Curtis ................... A61M 5/158 604/167.03 |
| 2010/0287793 A1 | 11/2010 | Hall et al. |
| 2011/0071476 A1 | 3/2011 | Mueller et al. |
| 2012/0058267 A1 | 3/2012 | Stueven et al. |
| 2012/0101577 A1 | 4/2012 | Lee |
| 2014/0039451 A1* | 2/2014 | Bangera ............... G06F 17/5086 604/506 |

* cited by examiner

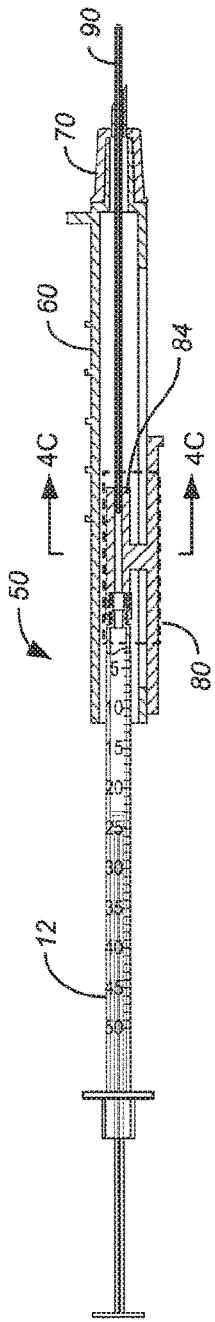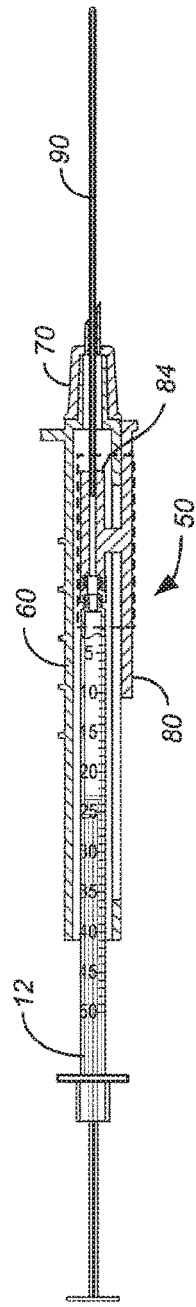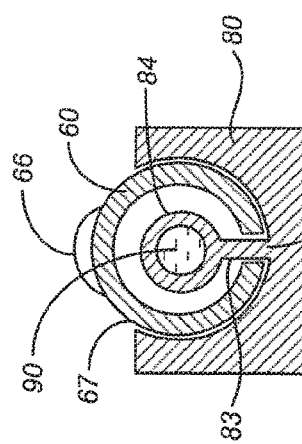

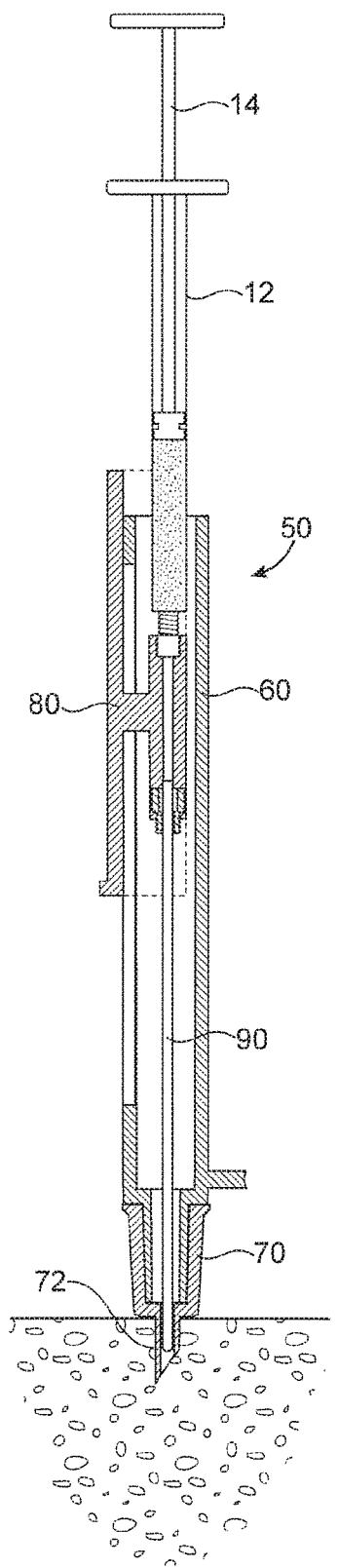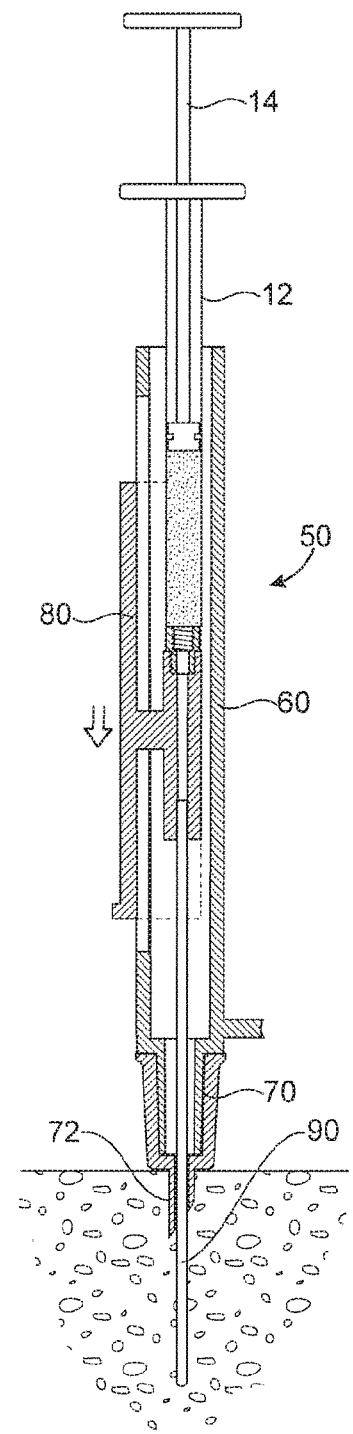
FIG. 6B
FIG. 6C

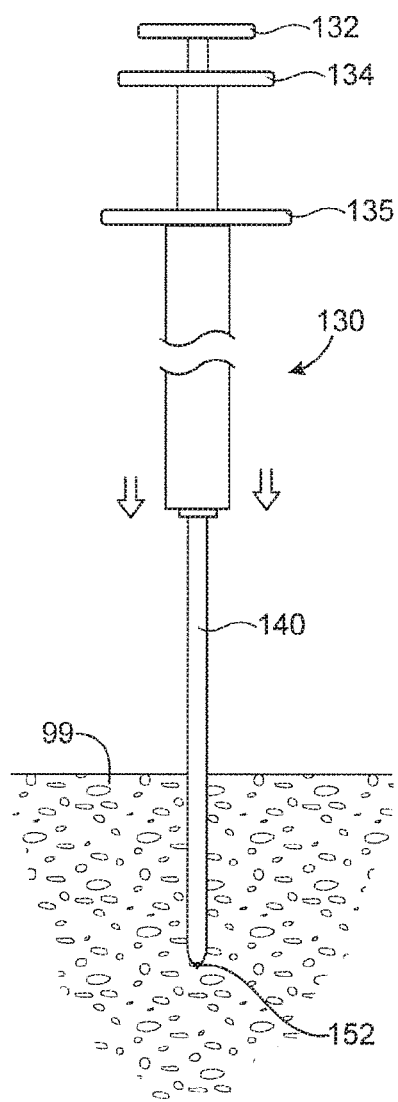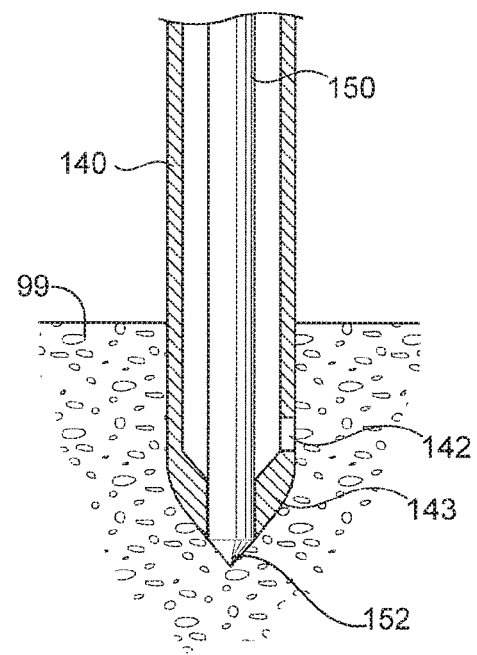
FIG. 8C
FIG. 8D

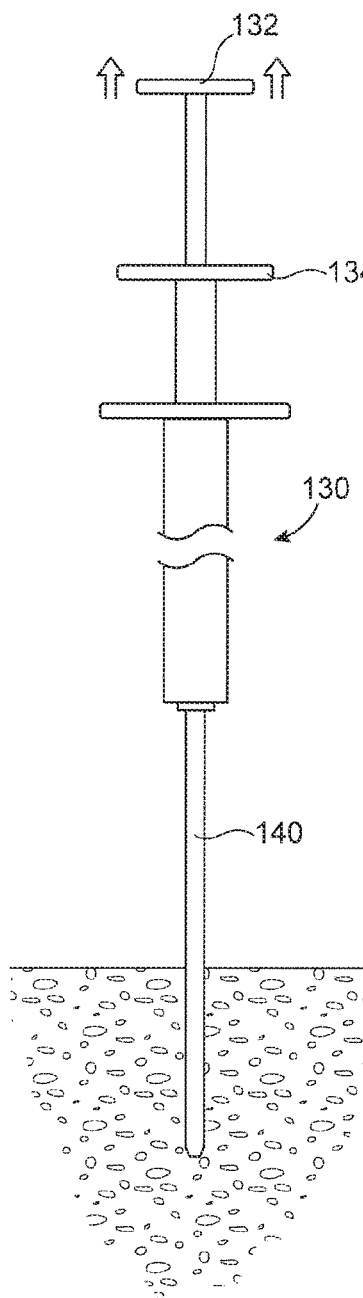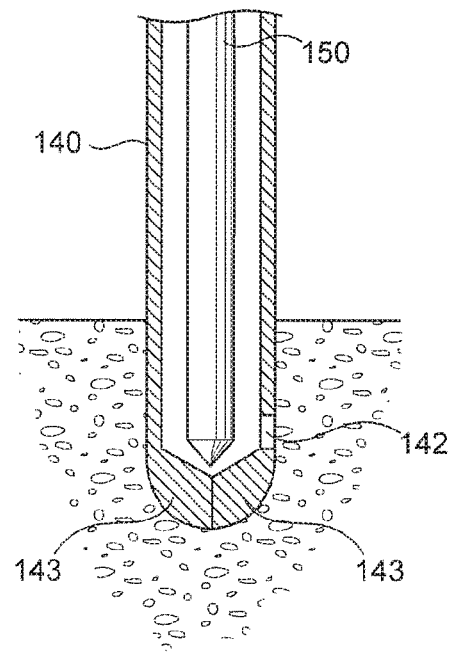
FIG. 8E
FIG. 8F

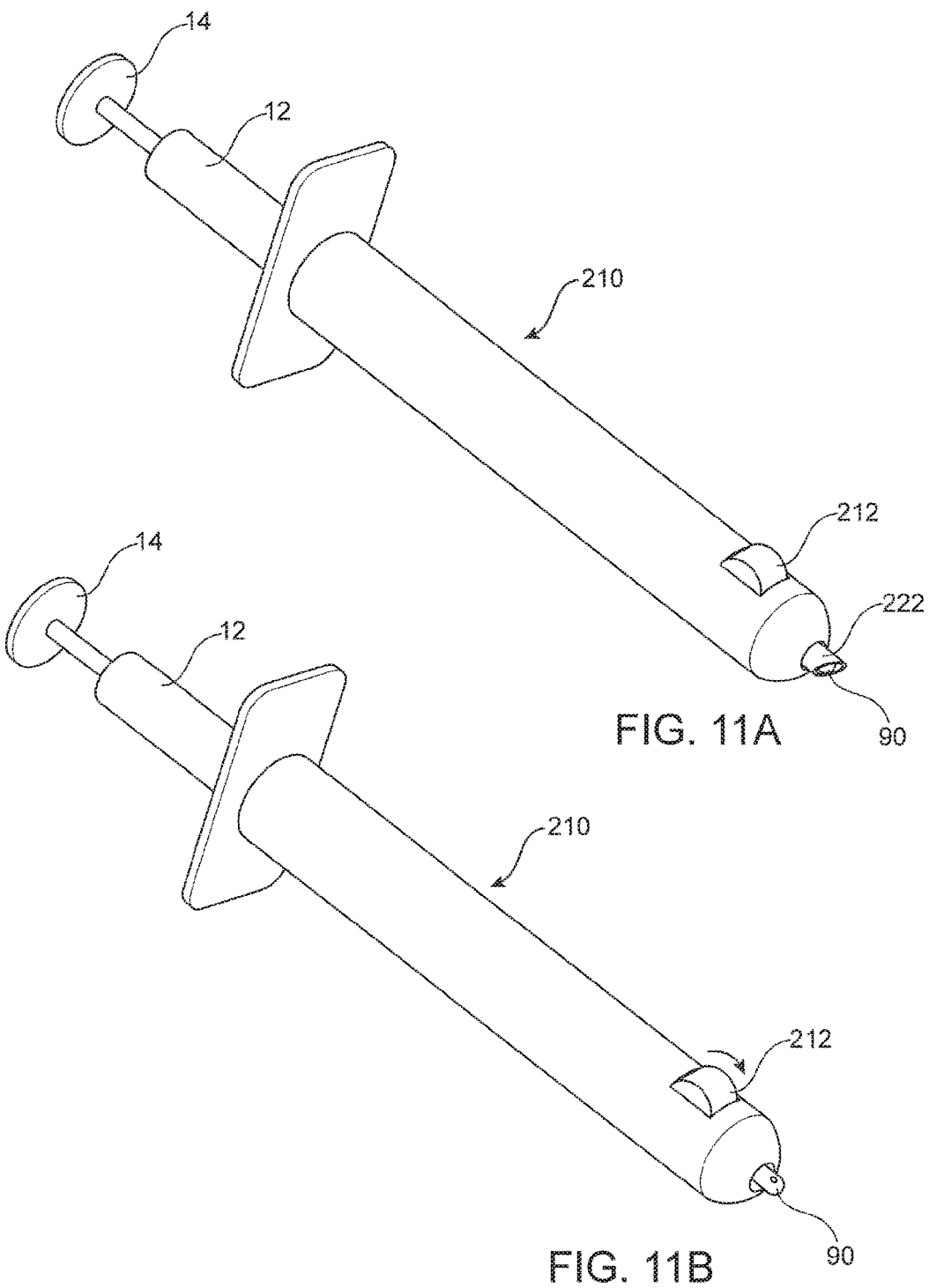

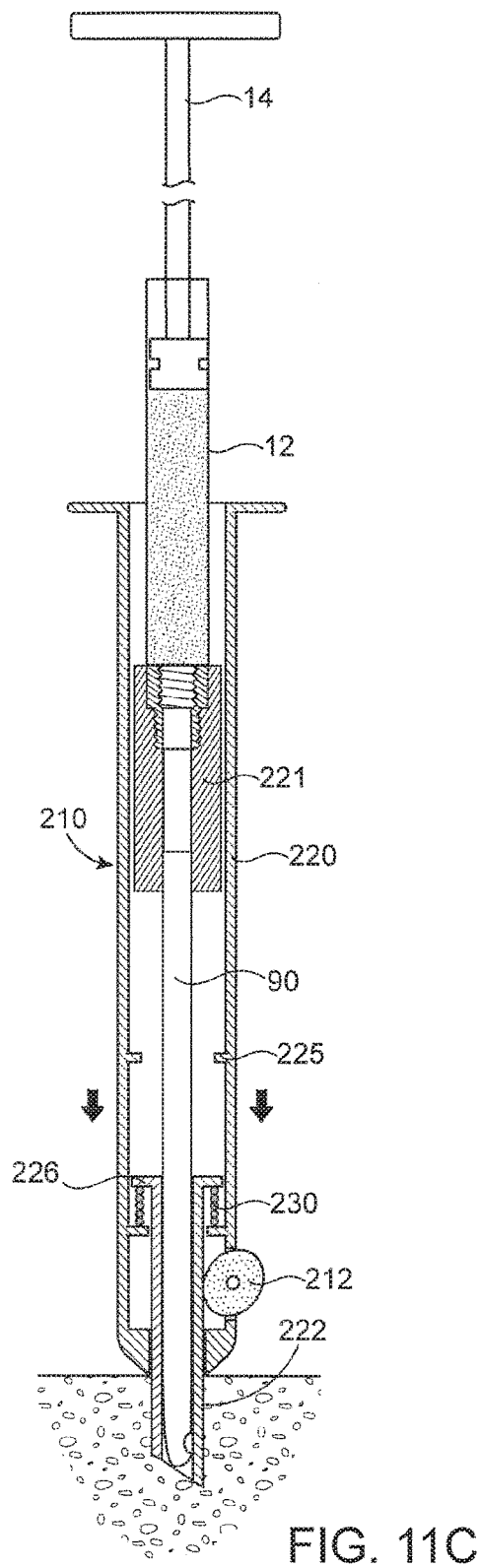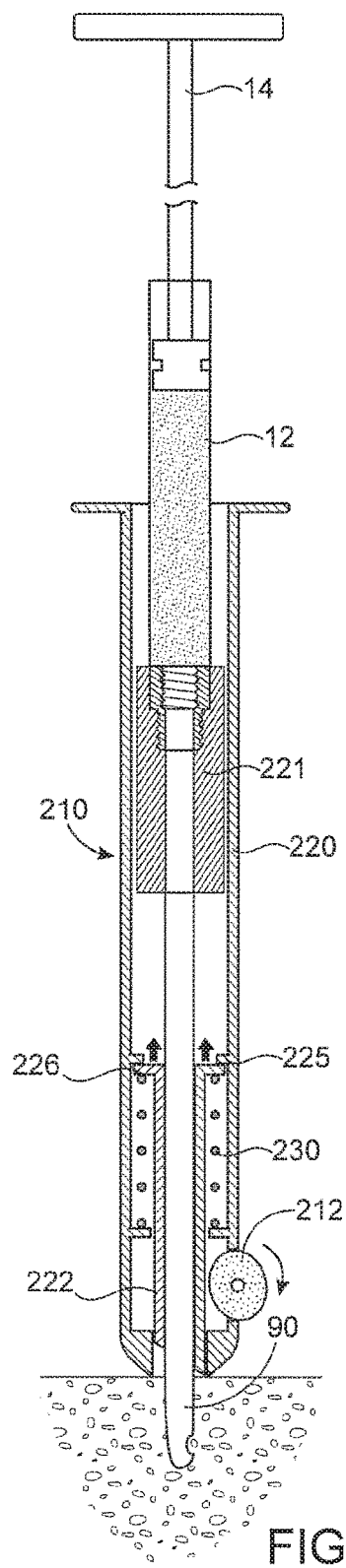

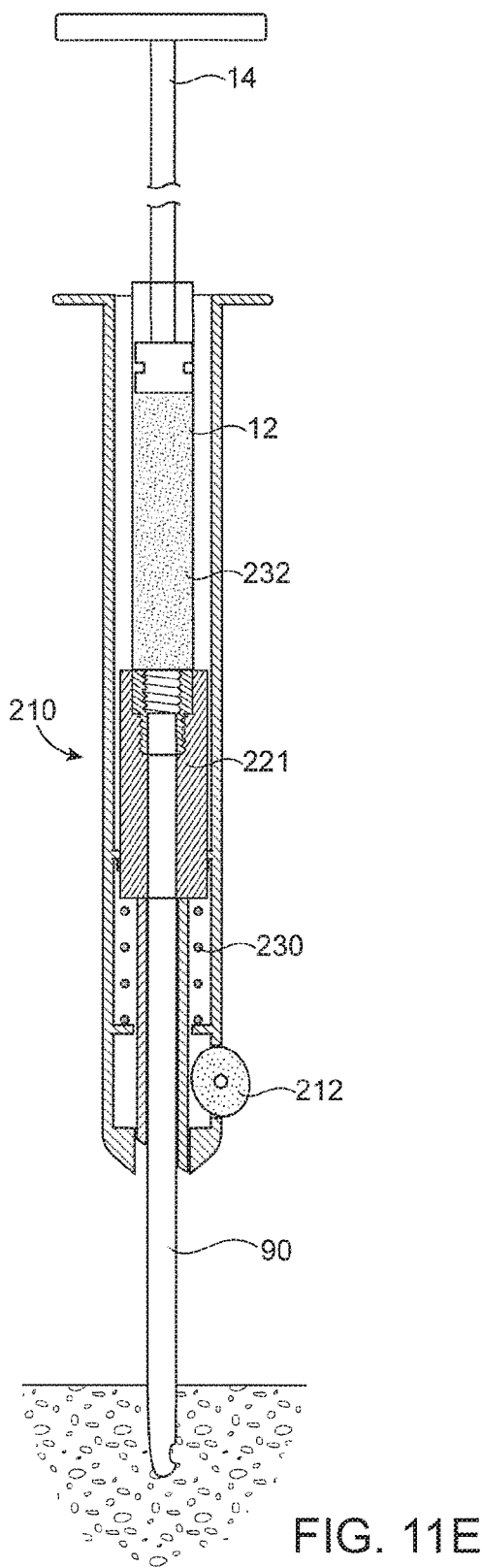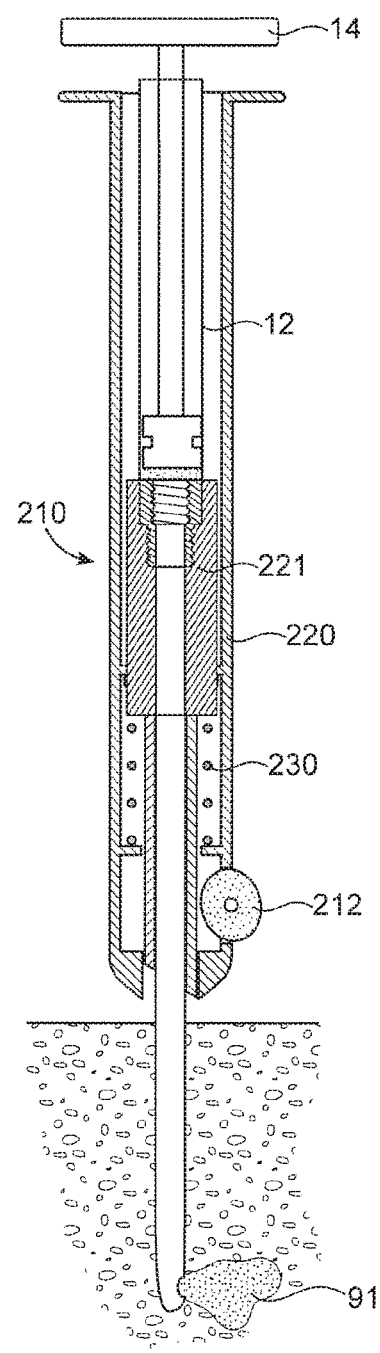
FIG. 11E
FIG. 11F

INTEGRATED NEEDLE AND CANNULA FOR PLASTIC SURGERY

CROSS-REFERENCE TO RELATED APPLICATIONS

This application claims the benefit of priority under 35 U.S.C. § 119(e) to U.S. Provisional Application No. 62/207,886, filed on Aug. 20, 2015, and entitled "Integrated Needle and Cannula For Plastic Surgery," the disclosure of which is hereby incorporated by reference in its entirety.

FIELD OF THE INVENTION

The present invention relates to medical instruments used by medical practitioners including Plastic Surgeons, Dermatologists, Otolaryngologists and mid-level medical practitioners. These medical instruments are used to inject substances beneath the skin including liquids and solid objects, such as threads. These injections are typically placed in the intra-dermal, sub-dermal, intra-muscular and/or sub-periosteal spaces.

BACKGROUND OF THE INVENTION

Plastic surgery, dermatology and otolaryngology involve medical procedures for improving and/or restoring the form and function of a body. Over the years, medical practitioners have developed a number of techniques and technologies to facilitate their art. From the earliest skin flap done by Tagliacozzi, the movement of tissue has benefited the form, appearance and function of patients. This tissue movement includes cosmetic and reconstructive procedures, such as breast augmentation, breast reconstruction, abdominoplasty, liposuction, nasal surgery, eyelid surgery and sub-dermal injections to restore tissue and volume.

Popular sub-dermal injections include injections of fillers, Botulinum Toxin ("Botox"), fat transfer and subcutaneous threads. Injections of sub-dermal substances are minimally invasive procedures to add substances, remove substances, stimulate tissues, lift tissues or tighten tissues to alter the contours of the face and body. Substances are also injected to dissolve fat and fillers. Common areas to inject sub-dermal substances are in the face, neck, hands, breasts and buttocks resulting in a contour change to create a restored, more youthful appearance. The types of injectable substances available include, but are not limited to, deoxycholic (bile) acid, hyaluronic acids, collagen-stimulating tumescent and autologous fillers (fat, platelet rich plasma), Botox, lidocaine, saline, hyaluronic acid fillers, synthetic wrinkle fillers (e.g., calcium hydroxyapatite, poly-1-lactic acid, poly glycolic acid), collagen wrinkle fillers, poly methyl methacrylate with bovine collagen, autologous wrinkle fillers, absorbable threads, non-absorbable threads and tumescent anesthesia solutions (collectively "medications" or "sub-dermal substances").

The most commonly used sub-dermal substances are hyaluronic acid fillers, collagen-stimulating fillers and Botox. Hyaluronic fillers are cross-linked hyaluronic acids typically used to naturally augment the lips and fill the areas of the face which lose volume with age, such as the temples, mid-cheek break, tear through, nasolabial fold and marionette lines. They are equally useful in men and women, although currently used more commonly in men. Hyaluronic acids are volumizing agents which typically last for six months to two years.

Collagen-stimulating fillers, such as sculptra poly-1-lactic acid, radiesse and calcium hydroxyapatite, are typically injected throughout the whole face to provide more structural volumizing. They typically last at least 18 months.

When injected, Botox blocks the nerve signals that cause muscles to contract. This effect relaxes and smoothes the look of lines and wrinkles caused by repetitive movements on the face—most commonly, between the brows (i.e., the frown), crows-feet around the eyes, and horizontal forehead creases. Botox is also used cosmetically to balance facial symmetry and relax tight neck bands, as well as medically to reduce perspiration, treat migraine headaches and treat muscle spasticity. Fat grafting is a procedure that involves the transfer of fat from areas where a patient has excess fat, such as the flanks and thighs, into areas that would benefit from added volume, stem cells or platelet rich plasma [PRP], such as the face, hands, breasts or buttocks.

Sub-dermal injections are typically performed using a needle attached to or coupled with a syringe. While a syringe with a sharp tipped needle is useful for penetrating a patient's skin, that same sharp tipped needle can cause significant bruising, vessel laceration, soft tissue necrosis and even blindness when the sharp needle transgresses vascular structures. Transgression of vascular structures is virtually unavoidable using a needle alone. For this reason, many medical practitioners prefer using a blunt tipped instrument, such as a blunt-tipped cannula, to administer sub-dermal substances to a patient. Nonetheless, since its tip is blunt, the blunt-tipped cannula is unable to readily penetrate the surface of the skin.

It is becoming increasingly popular for plastic surgeons and other medical practitioners to use a combination of a sharp-tipped needle (including a lancet, scalpel, trough or trocar) and a blunt-tipped cannula for their sub-dermal injections in a two-step process. First, the medical practitioner uses the sharp-tipped needle to puncture a hole in the patient's skin. The sharp-tipped needle is then withdrawn from the hole and the cannula is inserted into the hole so the substance can be delivered or withdrawn from within the subcutaneous space.

While this two-step process is simple in concept, it is not simple in application. For example, after the sharp-tipped needle is withdrawn from the patient's skin, it is often difficult for the medical practitioner to find the hole created by the sharp-tipped needle. He or she must also find a place to put the needle down. It can be awkward, time-consuming and embarrassing for the medical practitioner to hunt for the needle hole. Despite creating better aesthetic results for the patient with less risk, the current two-step needle-cannula process is more difficult for the medical practitioner to manage. As a result, many medical practitioners are reluctant to adopt the current two-step needle-cannula process and, instead, simply use a hypodermic needle attached to a syringe to administer sub-dermal substances. Although blunt-tipped cannula use for the administration of sub-dermal substances should become the standard of care for these procedures, the current technical and practical difficulties in using them in two un-integrated steps serves as an impediment to the adoption of the safer cannula technique.

What is needed is a way for medical practitioners to make injections quickly, easily and accurately using both a needle for puncturing the skin and a blunt-tipped cannula connected to a syringe for injecting the sub-dermal substances.

BRIEF SUMMARY OF THE INVENTION

The present invention provides a way for medical practitioners to inject sub-dermal substances with a single medical instrument in a way that is quick, easy and accurate, with all the patient and medical practitioner benefits that come with using a hypodermic needle (or a lancet, scalpel, trough or trocar) and a blunt-tipped cannula. In several preferred embodiments, a blunt-tipped cannula is chosen with a small enough diameter so it can slide through the annular space in a hypodermic needle. In this way, after the hypodermic needle penetrates into the patient's skin, the medical practitioner can slide the blunt-tipped cannula through the annular space of the needle and directly under the patient's skin. Once the blunt-tipped cannula is under the patient's skin, the hypodermic needle is withdrawn from the patient's skin to allow the injection to be made using only the blunt-tipped cannula.

In one preferred embodiment, the integrated needle and cannula of the present invention has a blunt-tipped cannula attached to the end of a syringe and threaded, at its distal end, through the annular space of a sharp-tipped hypodermic needle. With one hand, the medical practitioner inserts the hypodermic needle into the patient's skin and, with the other hand, the medical practitioner then slides the blunt-tipped cannula through the annular space of the needle and moves it underneath the patient's skin as the sub-dermal substance is being injected.

In a second preferred embodiment, the medical practitioner inserts a sharp trocar embedded in a soft holder into the patient's skin at desired locations. The surface of the holder that lies against the skin may have some adhesive or adherent substance that can help the holder adhere to the skin. After insertion, the medical practitioner withdraws the sharp trocar while leaving the soft holder in the patient's skin. Through the vacated trocar hole in the soft holder, the medical practitioner inserts the distal end of a blunt-tipped cannula. To insure an accurate injection, the medical practitioner should press down on the soft holder as the cannula is being inserted into the patient's skin. After the cannula is inserted, injections can be made using the blunt-tipped cannula.

In a third preferred embodiment, a transporter assembly is interposed between a syringe and an integrated hypodermic needle/cannula. The transporter assembly preferably includes a retractable inner needle tube or prong(s) attached to the hypodermic needle. The external transporter housing connects the syringe to the cannula, preferably through an integral cannula connector. As with the previous preferred embodiments, the blunt-tipped cannula in this transporter assembly embodiment is threaded through the annular space of the hypodermic needle. In operation, the medical practitioner first advances the inner needle tube forward until the hypodermic needle at its distal tip penetrates into the patient's skin. As the inner needle tube is advanced forward, it covers the full length of the blunt-tipped cannula and stabilizes the blunt-tipped cannula. After the hypodermic needle has penetrated into the patient's skin, the external transporter housing is advanced forward over the inner needle tube to cause the blunt-tipped cannula to slide through the needle and under the patient's skin. The inner needle tube is then pulled back to remove the needle from under the patient's skin, leaving only the blunt-tipped cannula in the skin. This can be accomplished manually by the medical practitioner or by using a triggering mechanism, such as a push or pull spring, that has been built into the device. The medical practitioner can then maneuver the blunt-tipped cannula under the patient's skin while injecting sub-dermal substances into the patient through the distal end of the blunt-tipped cannula.

In a fourth preferred embodiment, a sharp-tipped trocar is placed concentrically inside a blunt-tipped cannula so that the sharp end of the trocar protrudes from the distal end of the cannula. When the cannula is pressed against the patient's skin, the sharp tip of the trocar will penetrate into the patient's skin. The trocar is then fully or partially retracted from the cannula so that the cannula can be safely maneuvered under the patient's skin to inject sub-dermal substances. In one embodiment, the distal end of the cannula is fooled from a flexible, polymeric material that will seal up when the sharp end of the trocar is withdrawn.

The principles of the present invention are also applicable to thread-lift procedures, such as threaded face lifts. A dissolvable thread, such as a barbed, polydioxanone (PDO) thread, can be attached at one end to the distal end of the cannula. The remaining thread can then either be carried outside or inside the cannula. As in previous embodiments, a hypodermic needle is placed over the thread carrying cannula to puncture a hole in the skin. After the hole is made, the hypodermic needle is retracted. The threaded cannula needle is then advanced under the patient's skin to deposit the dissolvable thread.

BRIEF DESCRIPTION OF THE DRAWINGS

FIG. 4A is a side, cross-section view of the transporter assembly embodiment of FIG. 3 where the inner needle tube is extended partially forward.

FIG. 4B is a side, cross-section view of the transporter assembly embodiment of FIG. 3 where the inner needle tube is retracted backward.

FIG. 4C is a transverse, cross-section view of the FIG. 3 transporter assembly.

FIG. 6B is a side, cross-section view of the FIG. 6A transporter assembly embodiment after hypodermic needle insertion.

FIG. 6C illustrates how the blunt-tipped cannula can be inserted through the hypodermic needle and underneath the patient's skin using the FIG. 3 transporter assembly embodiment.

FIG. 8C illustrates insertion of the cannula and trocar distal tip into a patient's skin for the FIG. 8A embodiment.

FIG. 8D is a close-up, cross-section view of the FIG. 8A embodiment after the distal tip of the cannula and trocar have been inserted into a patient's skin.

FIG. 8E illustrates retraction of the trocar from the cannula's distal tip for the FIG. 8A embodiment.

FIG. 8F is a close-up, cross-section view of the FIG. 8A embodiment after the trocar has been retracted from the cannula's distal tip.

FIG. 11A illustrates an alternative push spring transporter assembly embodiment prior to release of the push spring.

FIG. 11B illustrates the alternative push spring transporter assembly embodiment of FIG. 11A after release of the push spring.

FIG. 11C is a cross-section view of the alternative push spring transporter assembly embodiment of FIG. 11A prior to release of the push spring.

FIG. 11D is a cross-section view of the alternative push spring transporter assembly embodiment of FIG. 11A after release of the push spring.

FIG. 11E is a cross-section view of the alternative push spring transporter assembly embodiment of FIG. 11A showing extension of the cannula.

FIG. 11F is a cross-section view of the alternative push spring transporter assembly embodiment of FIG. 11A illustrating insertion of sub-dermal substances.

DETAILED DESCRIPTION OF THE INVENTION

Figure 1:
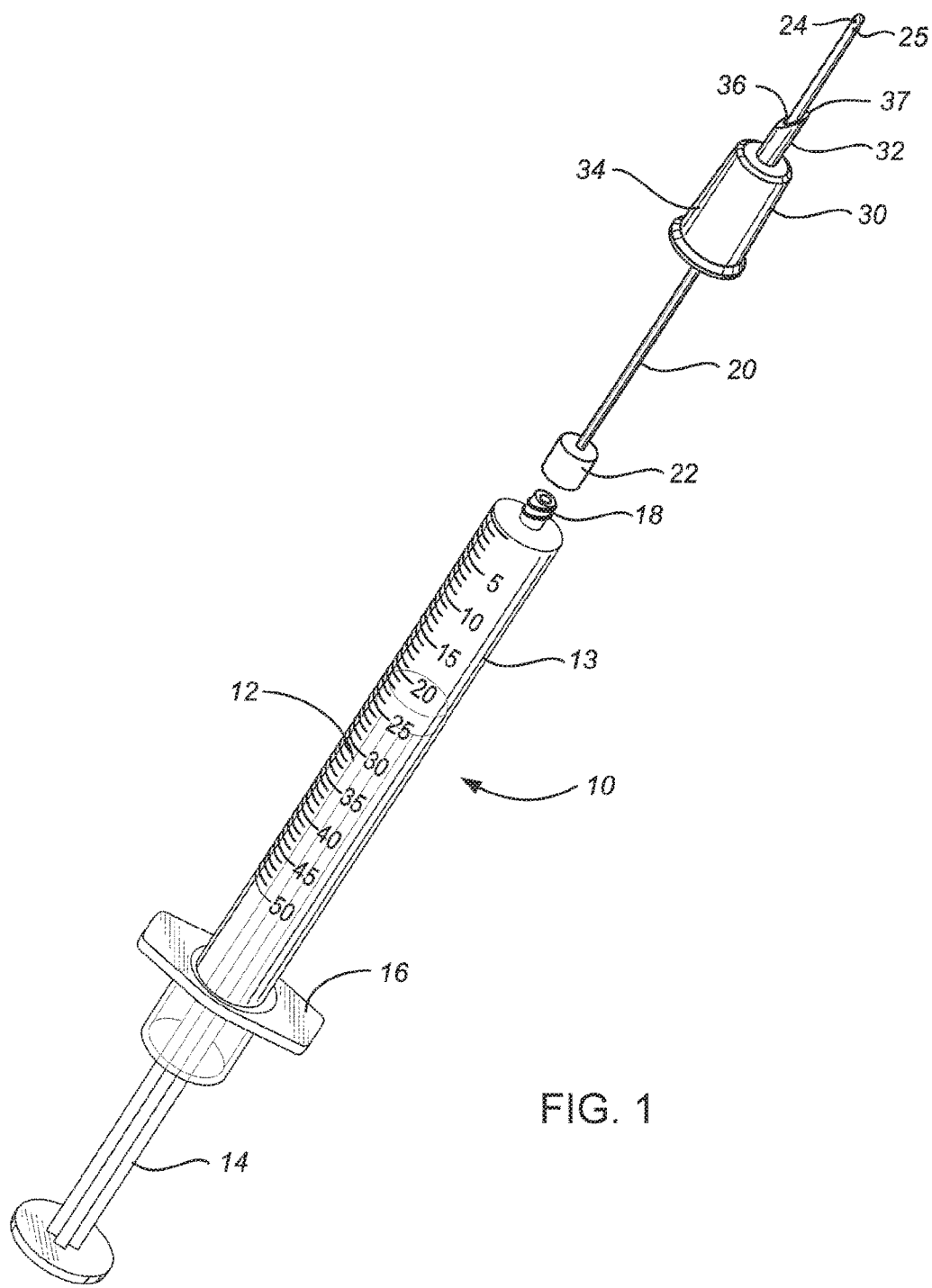
FIG. 1 is a perspective view of a first preferred integrated needle and cannula embodiment of the present invention.

Referring to FIG. 1, a first preferred embodiment of the integrated needle and cannula assembly 10 of the present invention is shown. This needle and cannula assembly 10 includes a syringe 12, a blunt-tipped cannula 20 and a hypodermic needle device 30. The syringe 12 in this embodiment is of conventional design with a generally cylindrical tube 13 to hold medication, a plunger 14 to squeeze out the sub-dermal substance, a finger grip 16 and the male portion of a connector 18, which is preferably a Luer Lock™ connector.

Attached to the syringe 12 in this preferred embodiment is a cannula 20. To securely attach the cannula 20 to the syringe 12, a female connector 22 is used, which is preferably a female Luer Lock™ connector capable of attaching to a male Luer Lock™ connector 18 on the syringe 12. The cannula 20 is preferably a blunt-tipped micro cannula that can be made in a wide range of lengths and gauges. For example, a typical length and gauge for sub-dermal substance application is 1.5 inches and 27 gauge. The type of cannula that can be attached to the syringe 12 includes the DermaSculpt™ micro cannulas produced by CosmoFrance, Inc., SoftFil™ micro cannulas produced by SoftFil-USA as well as micro cannulas produced by Kerylos Corporation and others. At the distal end 24 of the cannula 20, there are one or more holes 25 which allow medication to exit the cannula and be injected under the patient's skin. Blunt-tipped cannulas 20 are preferred for the present invention because they minimize the bruising, vessel lacerations and necrosis that can be associated with administration of medication, such as a sub-dermal filler, using a sharp hypodermic needle.

The hypodermic needle device 30 of this first preferred embodiment includes a needle holder 34 and needle 32. The needle holder 34 is preferably made from a hard, hypoallergenic plastic and the needle 32 is preferably made from metal, such as stainless steel or titanium with a sharp, beveled edge. The hypodermic needle device 30 preferably will be much shorter than the partner cannula 20 and must be long enough that, once advanced, it may penetrate the patient's epidermis and dermis. The present invention is applicable to many lengths and gauges of hypodermic needle 32. For example, a typical hypodermic needle 32 used for puncturing the skin for application of sub-dermal substances could be 27 gauge and 3 millimeters in length.

In the present invention, the hypodermic needle 32 needs to be of larger gauge than the cannula 20 so that the cannula 20 can slide into the annular space 36 formed inside the needle 32. For example, if a 25 gauge micro cannula were selected, the needle 32 could be approximately 27 gauge. The objective is to allow the cannula 20 to freely slide concentrically back and forth within the annular space 36 of the needle 32 without appreciable friction but with the smallest possible incision or hole in the patient's face. This is for the patient's comfort and optimal cosmesis. While the examples provided here involve a hypodermic needle tube, those of skill in the art will recognize that the hypodermic needle could be a partial tube or similar skin puncturing medical instrument.

In operation, the medical practitioner begins by pushing the distal end 37 of the hypodermic needle 32 with one hand until it is slightly beyond the distal end 24 of the cannula 20 while, at the same time, holding the syringe 12 with the other hand. The medical practitioner then inserts the needle 32 through the patient's skin at an appropriate location. After the needle 32 has penetrated into the patient's skin, the medical practitioner presses the syringe 12 forward to slide the cannula 20 through the needle 32 and under the patient's skin. The needle 32 is then withdrawn from the patient's skin while the distal end 24 of the cannula 20 remains under the patient's skin. To retain the needle 32 in the retracted position, a locking mechanism can be implemented between the needle holder 34 and the female connector 22, such as a friction fit or a screw lock (not shown). With the needle device 30 secured in a retracted position, the medical practitioner is now free to safely maneuver the cannula 20 under the patient's skin using the syringe 12 while pressing down on the syringe plunger 14 to administer medication.

Figure 2A:
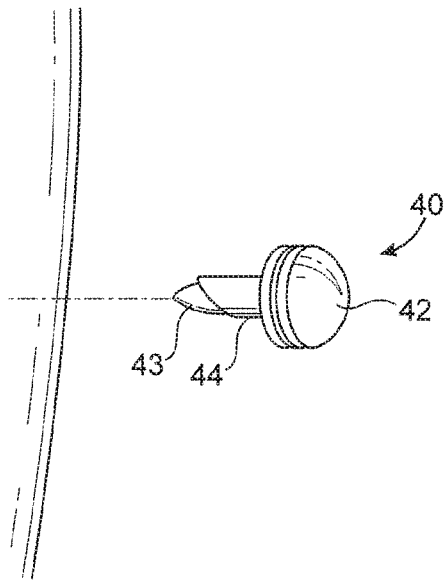
FIG. 2A illustrates a second preferred embodiment using a sharp trocar embedded in a soft holder.
Figure 2B:
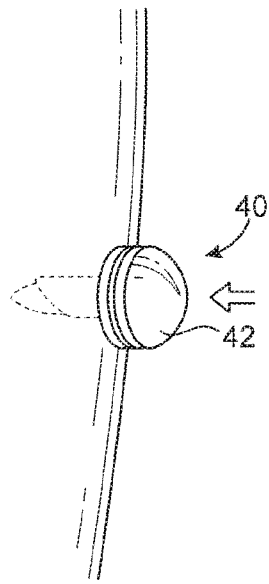
FIG. 2B illustrates the trocar embedded holder of FIG. 2A after it penetrates the patient's skin.
Figure 2C:
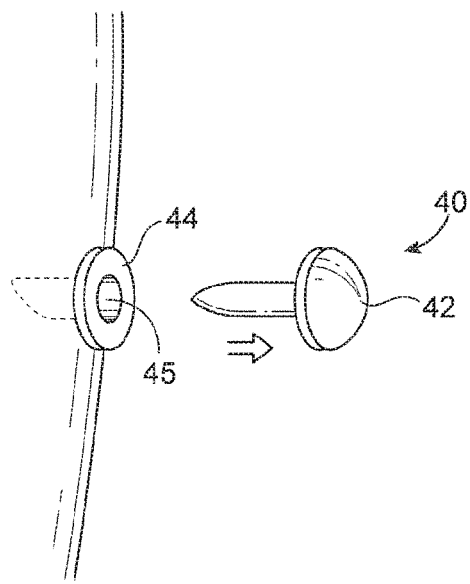
FIG. 2C shows removal of the trocar from the trocar embedded holder of FIG. 2A.
Figure 2D:
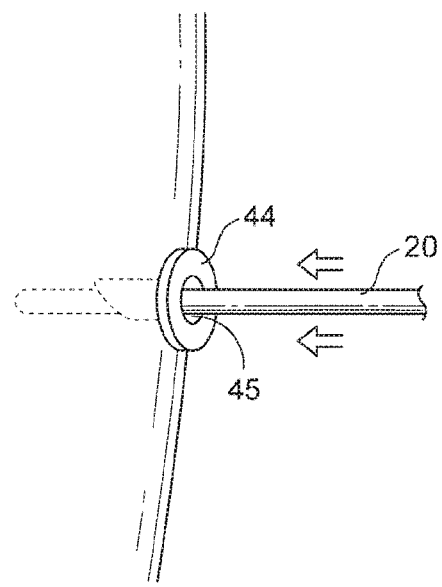
FIG. 2D shows insertion of a cannula into the FIG. 2A holder.
Figure 3:
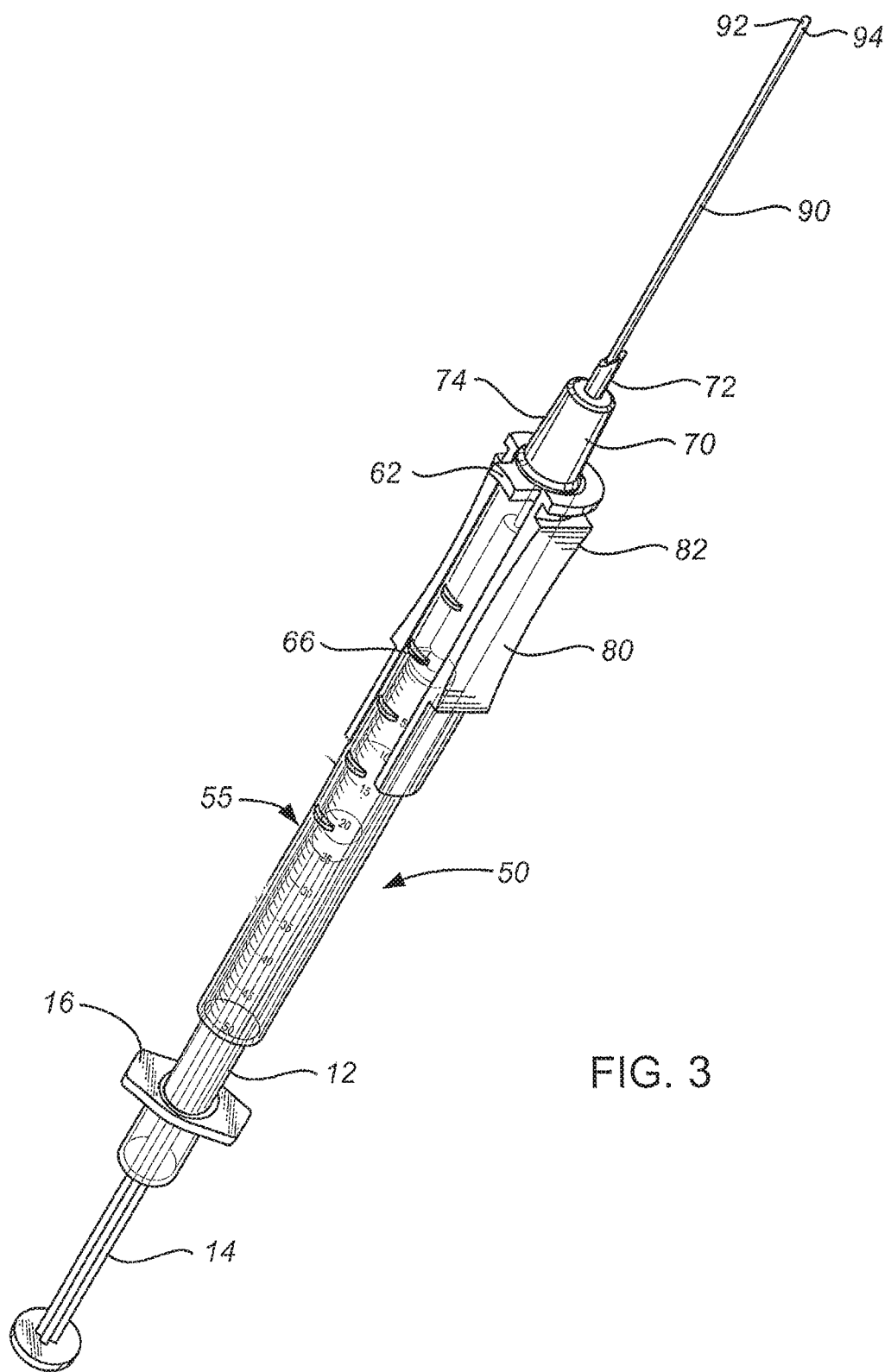
FIG. 3 illustrates a perspective view of a third preferred embodiment where a transporter assembly is interposed between a syringe and an overlapping hypodermic needle/cannula.

FIGS. 2A-2D illustrate a second preferred embodiment of the present invention. In this embodiment, a trocar embedded holder 40 is used which includes a sharp tipped trocar 42 and a soft holder 44. The soft holder 44 is preferably a small disk that can be made from rubber or plastic. The trocar 44 is preferably made from a hard metal such as stainless steel or titanium alloy. The objective of the trocar embedded holder 40 is to allow the medical practitioner, in one step, to create an entrance into the patient's skin in a way that allows ready insertion of a blunt-tipped cannula 20. To accomplish this objective, the soft holder 44 should be large enough for the medical practitioner to easily manipulate the blunt-tipped cannula 20, but small and lightweight enough that it will not fall off the patient's skin. In one embodiment, a disk is used for the soft holder 44 which is 1 cm in in diameter and ½ cm in thickness. The trocar 42 is initially attached to the soft holder 44 as shown in FIG. 2A. An adhesive or adherent substance may be applied to the soft holder 44 to aid in attachment to the patient's skin. In operation, one inserts the trocar embedded holder 40 into the patient's skin as shown in FIG. 2B by virtue of the sharp-tipped trocar 42. The trocar 42 is then withdrawn from the soft holder 44 as shown in FIG. 2C to provide on opening for the cannula 20. The cannula 20 is then inserted through the vacated central hole 45 in the soft holder 44 so that sub-dermal substances can be injected.

While a single trocar embedded holder 40 has been illustrated in FIGS. 2A-D, the medical practitioner may choose to use multiple trocar embedded holders 40 simultaneously. For example, the medical practitioner can place soft holders 44 at all the locations on a patient's face where collagen filler is to be injected. The medical practitioner can then use a syringe with cannula to readily go from soft holder 44 to soft holder 44 injecting a desired amount of collagen filler at each location. After collagen filler has been injected at one location, the soft holder 44 is removed before moving onto the next location.

Turning now to FIGS. 3-5B, a third preferred embodiment of the present invention is illustrated where the integrated needle and cannula 50 includes a transporter assembly 55 interposed between the syringe 12 and the concentric hypodermic needle 72/cannula 90. Because of the transporter assembly 55, the medical practitioner can insert the needle 72 using the same hand that is holding the syringe 12. This allows the medical practitioner to use their other hand to locate and prepare a port site on the patient's body for insertion of the needle 72.

Figure 5A:
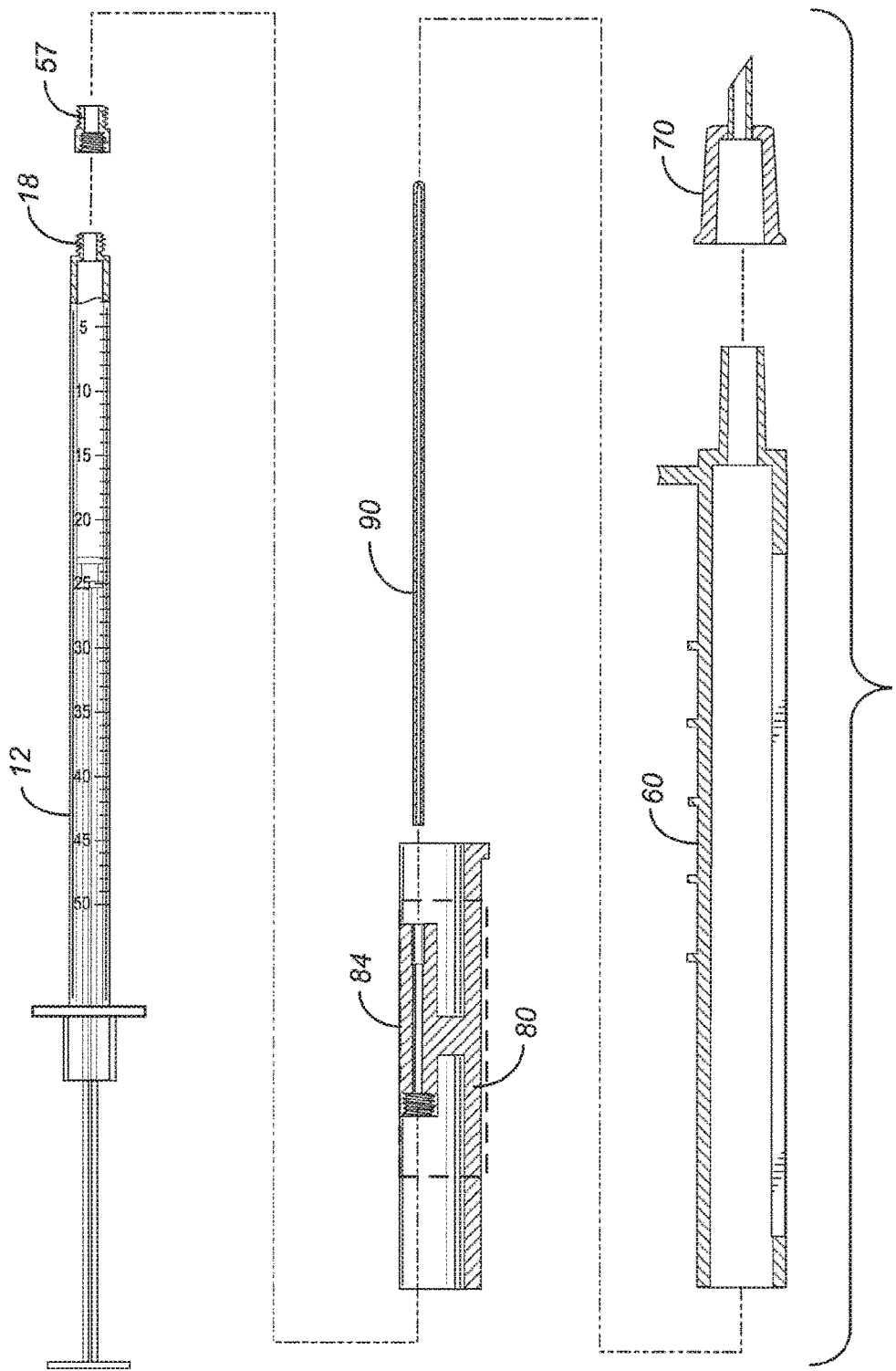
FIG. 5A is an exploded, side cross-section view of the FIG. 3 transporter assembly components.
Figure 5B:
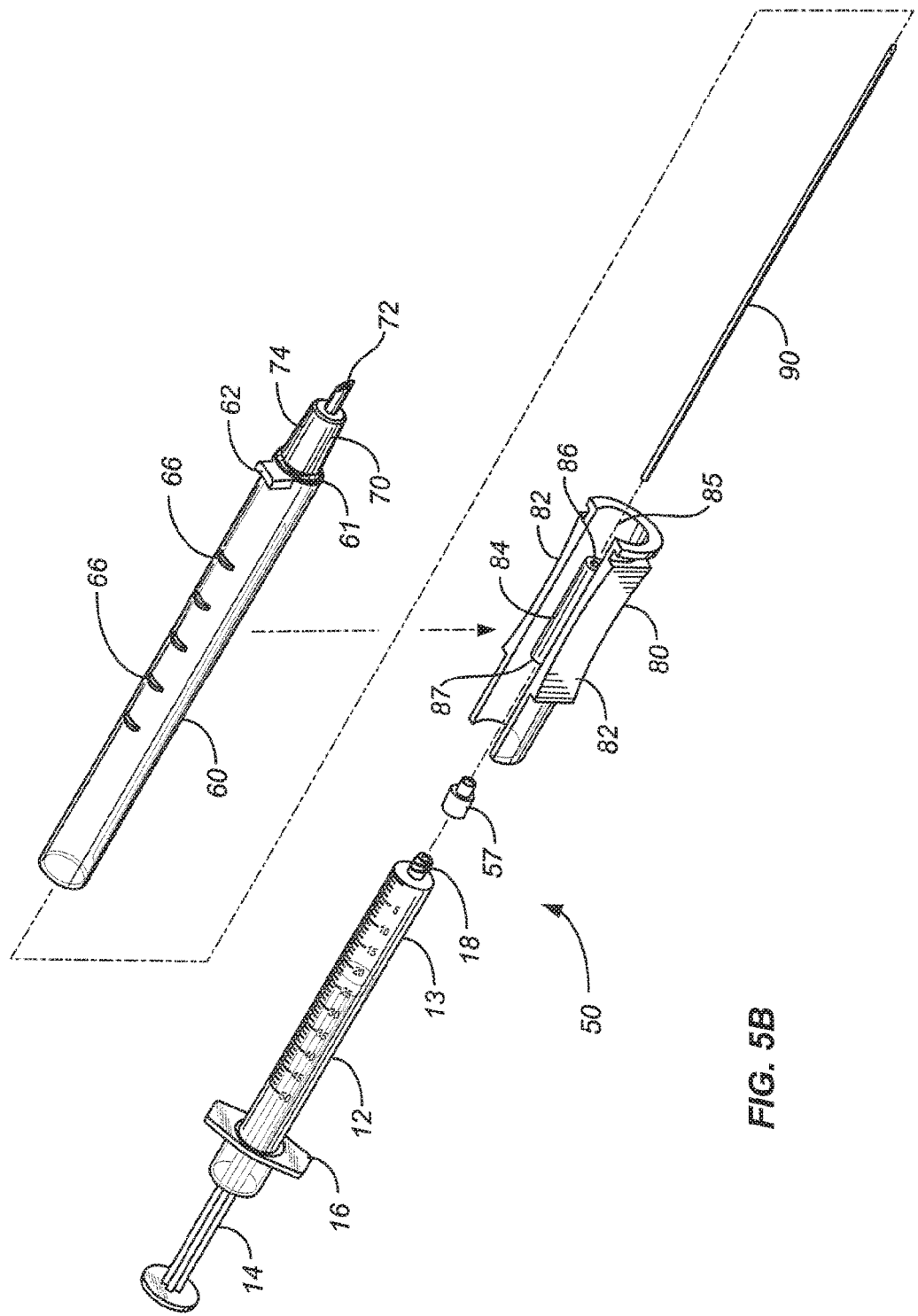
FIG. 5B is an exploded, perspective view of the FIG. 3 transporter assembly components.

As shown in FIG. 5B, the integrated needle and cannula with transporter assembly 50 includes a syringe 12, a retractable inner needle tube 60 with hypodermic needle device 70, an external transporter housing 80 and a cannula 90. The syringe 12 is preferably of the same type illustrated in FIG. 1 with a generally cylindrical tube 13 to hold the sub-dermal substance, a plunger 14, a finger grip 16 and the male portion of a connector 18, which is preferably a Luer Lock™ connector. Through its male connector 18, the syringe 12 attaches to the external transporter housing connector 84 inside the external transporter housing 80. This external transporter housing connector 84 preferably includes a connector tip 57 which mates directly with the syringe connector 18. For example, where the syringe connector is a male Luer Lock™ connector, the connector tip 57 inside the external transporter housing 80 would be a mating female Luer Lock™ connector.

In the preferred embodiment, the external transporter housing 80 is generally cylindrical in shape and, apart from its internal connector 84, is generally hollow inside. The purpose of the internal connector 84 of the external transporter housing 80 is to connect the syringe 12 to the external transporter housing 80 at the proximal end 87 of the internal connector 84 and connect the cannula 90 to the external transporter housing 80 at the distal end 86 of the internal connector 84. The external transporter housing 80 is preferably made from a hard plastic, but could also be made from other materials, such as stainless steel or titanium. On each side of the external transporter housing 80 is a finger grip 82. The finger grips 82 allow the external transporter housing 80 to be held and manipulated more easily.

Inserted within the hollow interior annular space 85 of the external transporter housing 80 is the retractable needle tube 60. Like the external transporter housing 80, the inner tube 60 is preferably made from a hard plastic, but could also be made from other materials, such as stainless steel. At its distal end 61, the retractable inner needle tube 60 is attached to the needle holder portion 74 of a hypodermic needle device 70. The purpose of the retractable inner needle tube 60 is to slide the hypodermic needle 72 backward and forward within the external transporter housing 80. To aid in moving the inner needle tube 60, a tab 62 and multiple bumps 66 are placed on top of the inner needle tube 60

As best shown in FIG. 4C, the inner needle tube 60 is placed concentrically inside the external transporter housing 80. A longitudinal gap 65 is formed on the bottom of the inner needle tube 60 to accept the base 83 of the external transporter housing connector 84. In addition to allowing the connector 84 to properly align the syringe 12 and cannula 90, this connector base 83 acts as a track to hold the inner needle tube 60 in place and prevent it from wobbling as it moves backward and forward.

As in the previous preferred embodiments, the gauge of the needle 72 of the hypodermic needle device 70 should be larger than the cannula 90 gauge so that the cannula 90 can slide concentrically through the interior annular space of the needle 72. In this embodiment, the transporter assembly 55 assists with the concentric movement of the cannula 90 with respect to the needle 72 so the medical practitioner does not have to worry about threading the cannula 90 into the annular space of the needle 72.

Figure 6A:
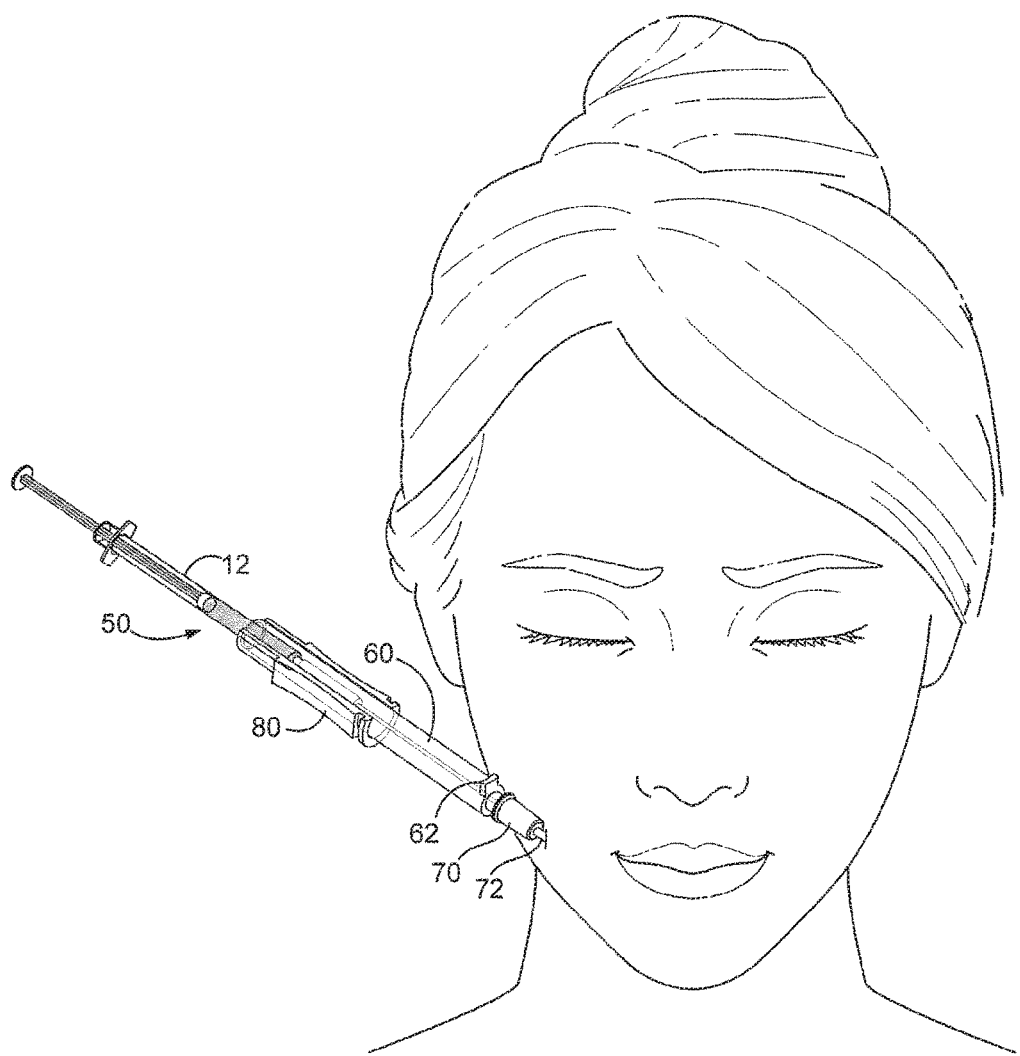
FIG. 6A illustrates insertion of the hypodermic needle from the FIG. 3 transporter assembly embodiment into a patient's skin.

FIGS. 6A-6E illustrate how the integrated needle and cannula with transporter assembly 50 can be used by a medical practitioner to easily and comfortably inject the sub-dermal substance into a patient. The medical practitioner first pushes the inner needle tube 60 and, with it, the hypodermic needle 70 forward until the inner needle tube 60 completely encloses the cannula 90 (see, FIG. 6B). To enhance reliability, it is preferable that the inner needle tube 60 locks onto the external transporter housing 80 when the inner needle tube 60 is in this extended position. The locking can be accomplished, for example, by creating a latch, slide or other locking mechanism (not shown) at the interface between the inner needle tube 60 and the external transporter housing 80. After the inner needle tube 60 and hypodermic needle 72 are extended forwardly, the medical practitioner inserts the hypodermic needle 72 into the patient at an appropriate location as shown in FIGS. 6A-B.

Using the finger grips 82, the medical practitioner then pushes the external transporter housing 80 forward as shown in FIG. 6C which has the effect of moving the cannula 90 through the annular space of the concentric hypodermic needle 72 and underneath the patient's skin. Moving the external transporter housing 80 forward as shown in FIG. 6C also has the effect of retracting the inner needle tube 60 into the external transporter housing 80.

Figure 6D:
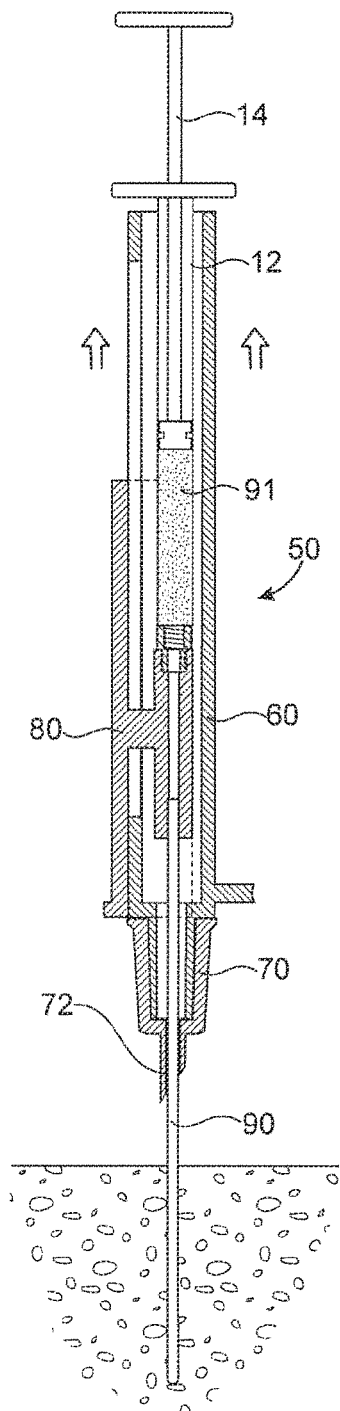
FIG. 6D illustrates how the hypodermic needle is retracted while the blunt-tipped cannula remains under the patient's skin for the FIG. 3 transporter assembly embodiment.
Figure 6E:
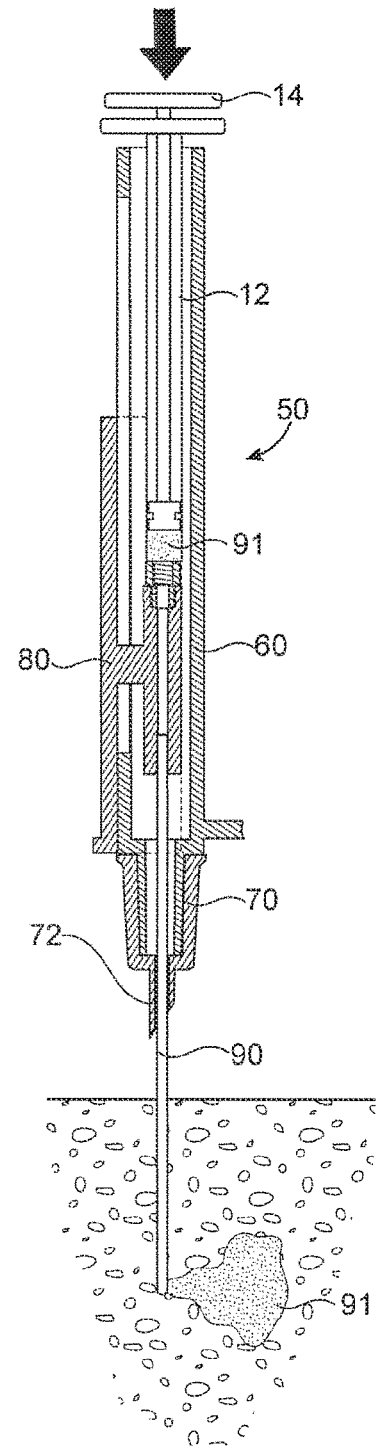
FIG. 6E illustrates how medication is inserted into the patient using the syringe in the FIG. 3 transporter assembly embodiment.

As shown in FIG. 6D, the medical practitioner then pulls the hypodermic needle 72 and transporter assembly 55 backward to remove the hypodermic needle 70 from the patient while leaving the cannula 90 under the patient's skin. The medical practitioner is then ready to inject the sub-dermal substance 91 into the patient by pressing down on the syringe plunger 14 as shown in FIG. 6E. As desired, the medical practitioner can move the cannula 90 around underneath the patient's skin while the sub-dermal substance is being injected to insure that the sub-dermal substance is being evenly distributed.

FIGS. 7A-E illustrates an integrated hypodermic needle/cannula 100 with a simplified transporter assembly. As in the FIG. 1 embodiment, the syringe 12 is attached directly to the cannula 92 here, preferably with a Luer Lock™ type mechanism. In this embodiment, the transporter assembly features a two-pronged hypodermic needle holder 120 and a mating prong receiver 110 formed on or attached to the syringe 12. Both the hypodermic needle holder 120 and the prong receiver 110 are preferably made from a hard, medical plastic. The hypodermic needle holder 120 consists of an outward facing hypodermic needle 128, a base 126 holding the hypodermic needle and one or more prongs 122 attached to the base 126. In the preferred embodiment shown in FIGS. 7A-E, two prongs 122 are used. Each of the prongs 122 is sized to fit into the longitudinal interior space 111 of a prong receiver 110. In the preferred embodiment, holes 114, 118 are preferably formed on the outer facing wall 116 of each prong receiver 110. The holes are sized to fit bumps 124 which are formed at the proximal end of each prong 122.

Figure 7A:
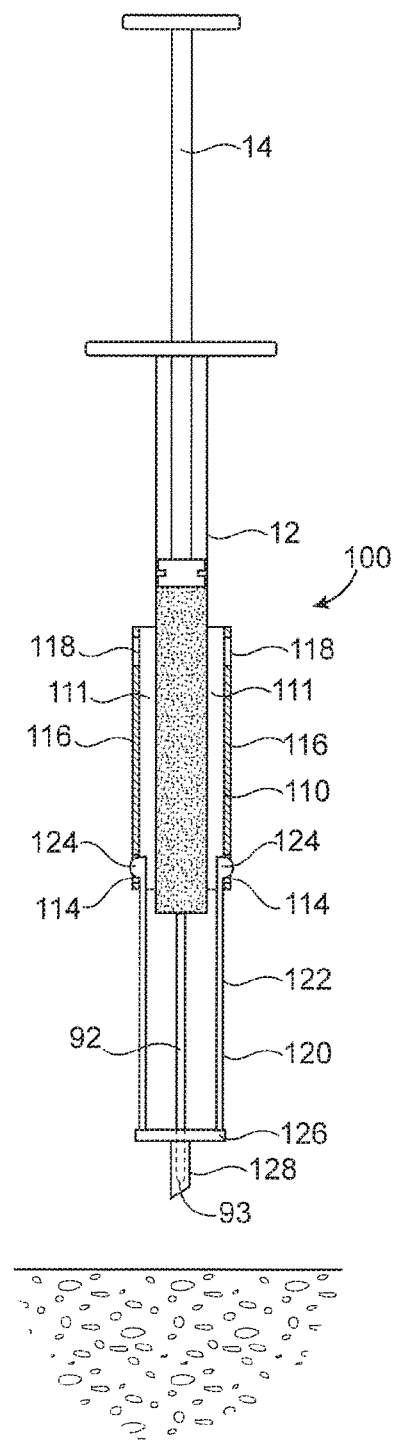
FIG. 7A is a side, cross-section view occurring prior to hypodermic needle insertion of an alternative transporter assembly embodiment where the hypodermic needle is attached to two prongs rather than an inner needle tube.
Figure 7B:
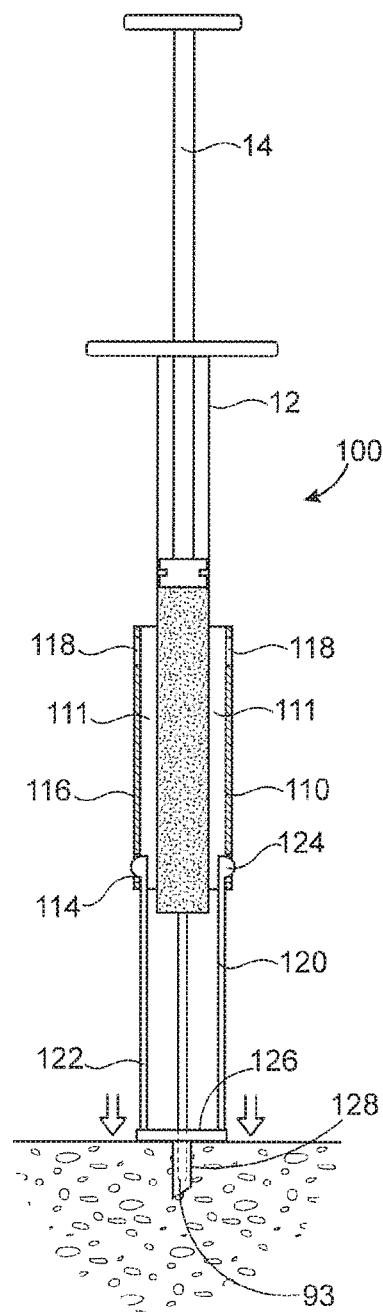
FIG. 7B is a side, cross-section view of the two-pronged alternative embodiment of FIG. 7A after the hypodermic needle penetrates a patient's skin.
Figure 7C:
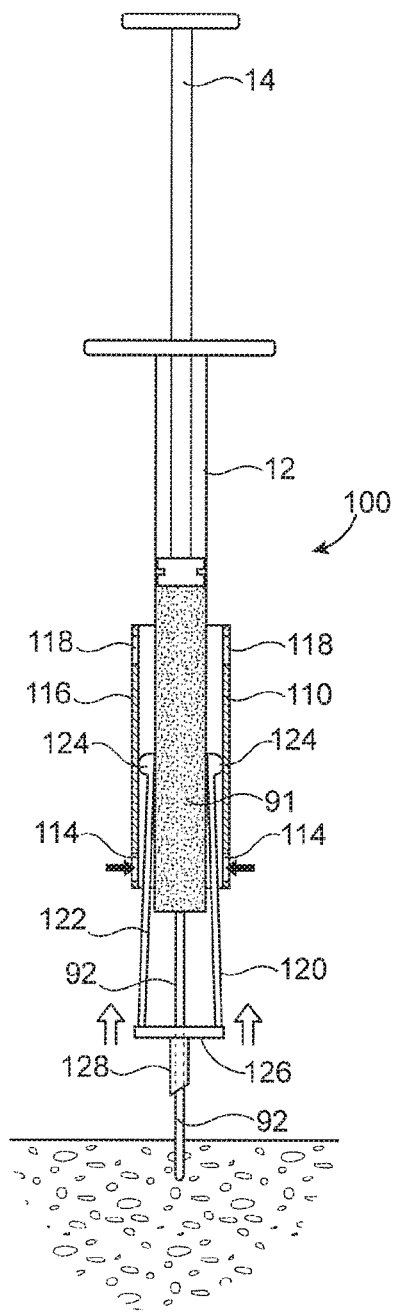
FIG. 7C is a side, cross-section view of the two-pronged alternative embodiment of FIG. 7A illustrating partial retraction of the hypodermic needle.
Figure 7D:
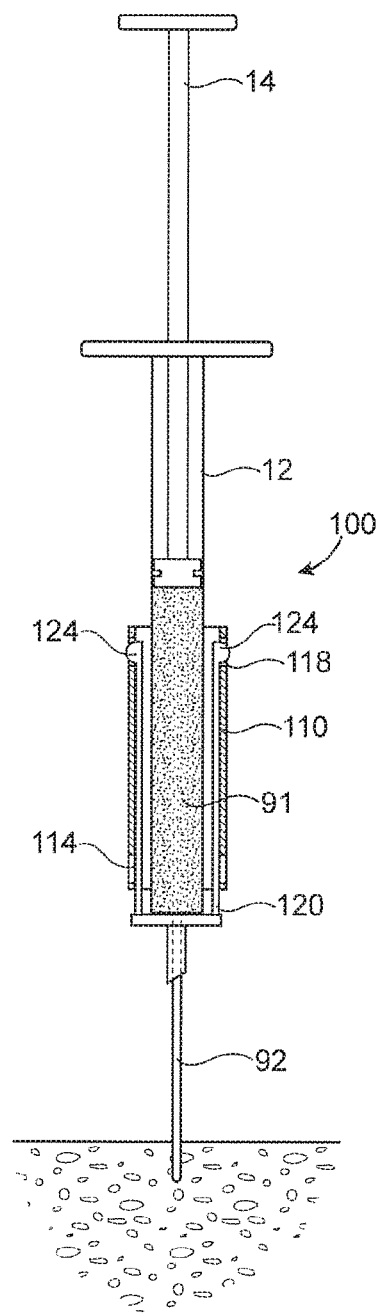
FIG. 7D is a side, cross-section view of the two-pronged alternative embodiment of FIG. 7A illustrating full retraction of the hypodermic needle.
Figure 7E:
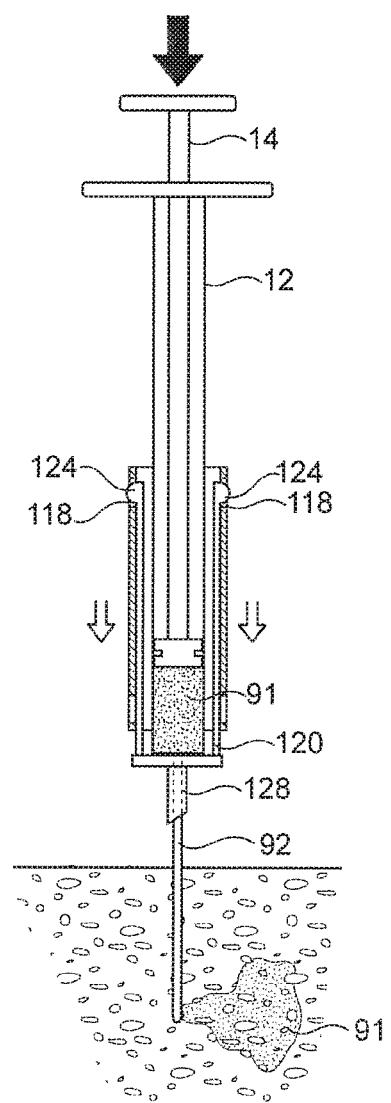
FIG. 7E is a side, cross-section view of the two-pronged alternative embodiment of FIG. 7A illustrating injection of sub-dermal substances using the cannula.

The purpose of the holes 114, 118 and bumps 124 are to allow the hypodermic needle holder 120 to be secured in either a forward position (FIGS. 7A-B) or a retracted position (FIGS. 7D-E).

In operation, the integrated hypodermic needle/cannula 100 starts with the hypodermic needle holder 120 secured in its forward position as shown in FIGS. 7A-B. In this forward position, the hypodermic needle 128 covers and protrudes past the distal tip 93 of the cannula 92. This allows the hypodermic needle 128 to penetrate into the patient's skin. To keep the hypodermic needle 128 steady as it is penetrating into the patient's skin, the bumps 124 of prongs 122 are received into the forward holes 114 of the prong receiver 110. FIG. 7B shows the hypodermic needle 128 penetrating into the patient's skin while the prongs 122 are in a forward, secured position. Once the hypodermic needle 128 has made an introducer hole in the patient's skin, it is retracted as shown in FIG. 7C. In the preferred embodiment shown, retraction is simply a matter of pressing the bumps 124 out of the forward holes 114 to release the prongs 122 and pulling the prongs 122 upward. The prongs 122 should continue to be pulled upward until the bumps 124 click into the rear holes 118 of the prong receiver 110 as shown in FIG. 7D. At this point, the two-pronged hypodermic needle holder 120 is secured into its fully retracted position and remains stationary as sub-dermal substances 91 are injected through the cannula 92 and into the patient by pressing down on the syringe plunger 14, as shown in FIG. 7E.

Figures 8A, 8B:
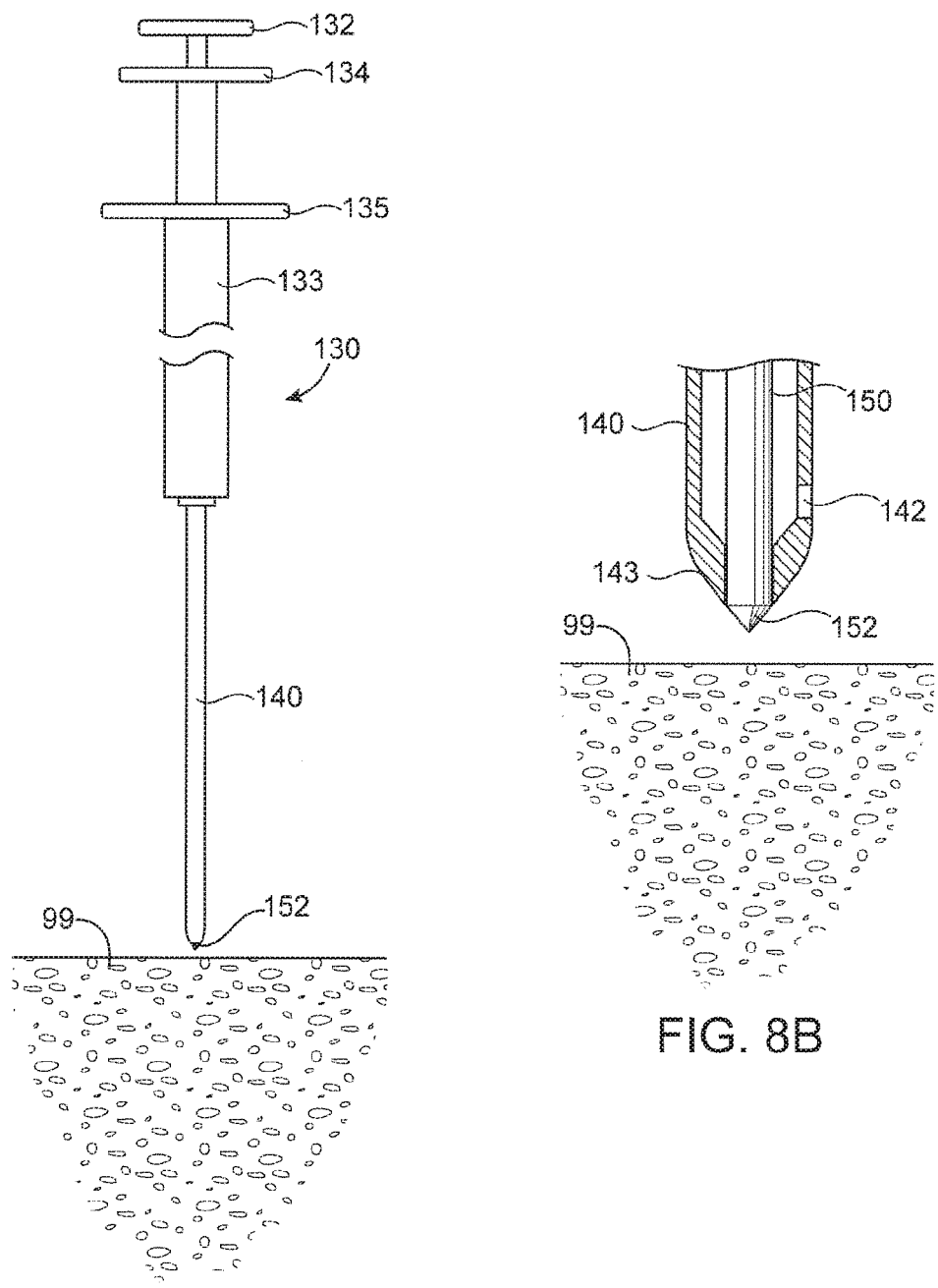
FIG. 8A illustrates a preferred integrated cannula and trocar embodiment of the present invention.
FIG. 8B is a close-up, cross-section view of the distal tip of the cannula and trocar embodiment of FIG. 8A.

FIGS. 8A-H illustrate an integrated cannula/trocar 130 preferred embodiment of the present invention. Unlike the earlier integrated hypodermic needle/cannula embodiments, the needle which punctures the skin in this embodiment is inside the cannula rather than outside the cannula. As shown in FIG. 8A, the syringe 133 in this embodiment is attached directly to the cannula 140 in a manner similar to the FIGS. 1 and 7A-E embodiments. Nonetheless, the syringe 133 in this embodiment differs from the syringe 12 in the FIGS. 1 and 7A-E embodiments because it includes a sharp-ended trocar 150 as well as a plunger 132 for manipulating the trocar 150 up and down within the syringe 133. Like the FIGS. 1 and 7A-E embodiments, the syringe 133 in this embodiment has a plunger 134 for dispensing sub-dermal substances into the patient. In this preferred embodiment, the trocar plunger 132 is concentrically inside the sub-dermal substance plunger 134. Alternatively, those of skill in the art will recognize that the trocar plunger can be configured to be concentrically outside the sub-dermal substance plunger.

Figure 8G:
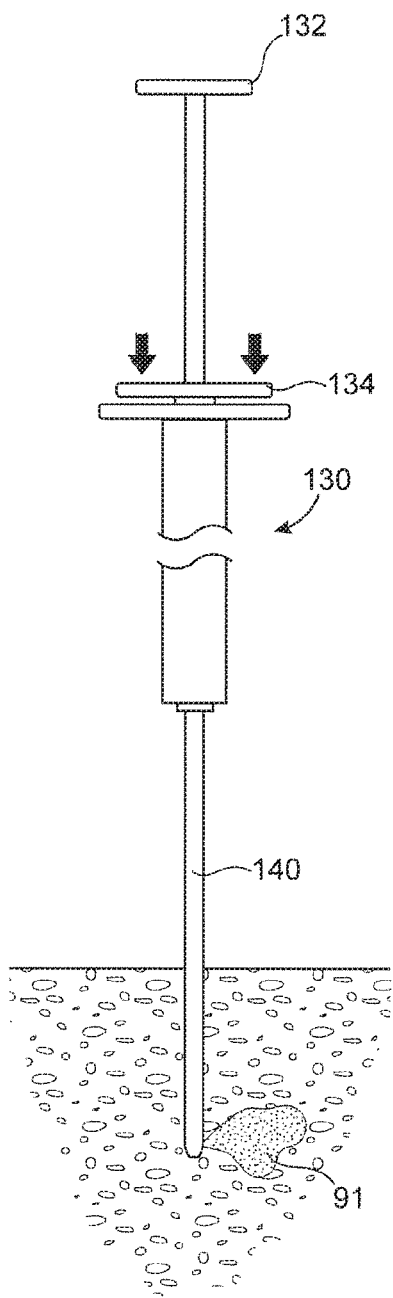
FIG. 8G illustrates insertion of sub-dermal substances for the FIG. 8A embodiment after the trocar has been retracted from the cannula's distal tip.
Figure 8H:
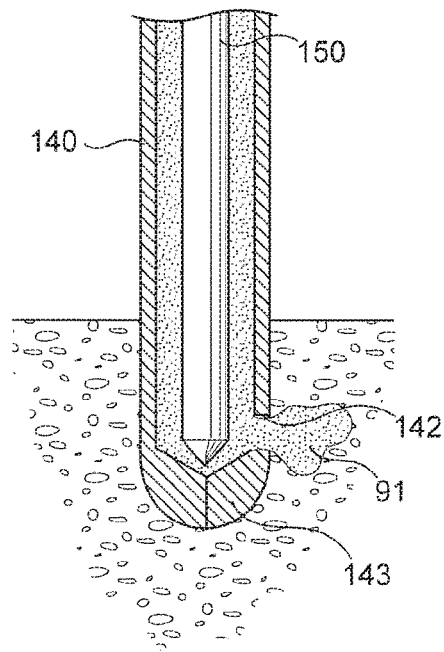
FIG. 8H is a close-up, cross-section view of the FIG. 8A embodiment illustrating insertion of sub-dermal substances after the trocar has been retracted from the cannula's distal tip.

In operation, as illustrated in FIGS. 8A-B, the sub-dermal substance plunger 134 of the syringe 133 starts in its fully retracted position while the trocar plunger 132 starts in its fully forward position. The trocar plunger 132 starts in its fully forward position so that the tip 152 of the trocar 150 will be fully forward and protruding out of cannula tip 143 as shown in FIG. 8B. In this starting position, it is preferable that the trocar plunger 132 and trocar tip 152 be temporarily locked in place so they will not move when the trocar tip 152 is used to puncture a hole in the patient's skin 99 as shown in FIGS. 8C-D. This locking can be accomplished, for example, with a twist or screw lock. To facilitate penetration into the patient's skin 99, the trocar 150 is preferably made from stainless steel or a medical grade metal alloy (e.g., nickel titanium alloy) and provided with a sharpened tip 152. Once a puncture hole is made in the patient's skin 99, the trocar plunger 132 is pulled upward (e.g., after unlocking) as shown in FIGS. 8E-F to retract the trocar 150 within the cannula 140. In one preferred embodiment, the cannula tip 143 is made from a flexible memory polymer which will re-seal itself as shown in FIG. 8F as the trocar 150 is withdrawn. To the extent the cannula tip 143 reseals itself, this allows sub-dermal substance 91 to be dispensed through a side hole 142 near the distal cannula tip 143 as shown in FIGS. 8G-H as the sub-dermal substance plunger 134 is pressed downward. Otherwise, sub-dermal substance 91 can be dispensed through the cannula tip 143 to the extent it does not reseal itself.

FIGS. 9A-B, 10A-B and 11A-G illustrate three integrated hypodermic needle/cannula embodiments where a spring mechanism is used to automatically retract the hypodermic needle after it has penetrated into the patient's skin. The spring retraction mechanisms allow the medical practitioner to easily operate the integrated hypodermic needle/cannula with one hand while keeping the other hand free. With a free hand, for example, the medical practitioner can touch the patient's skin to prepare the patent's skin for injection or find an optimal entry point.

Figure 9A:
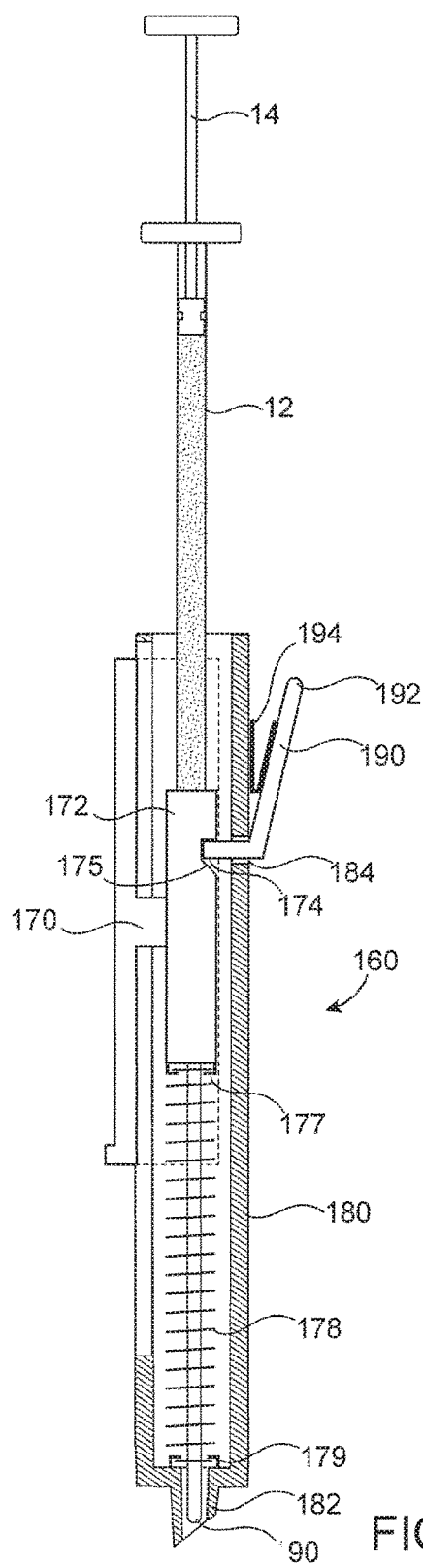
FIG. 9A is a cross-section view of a pull spring transporter assembly embodiment prior to release of the pull spring.
Figure 9B:
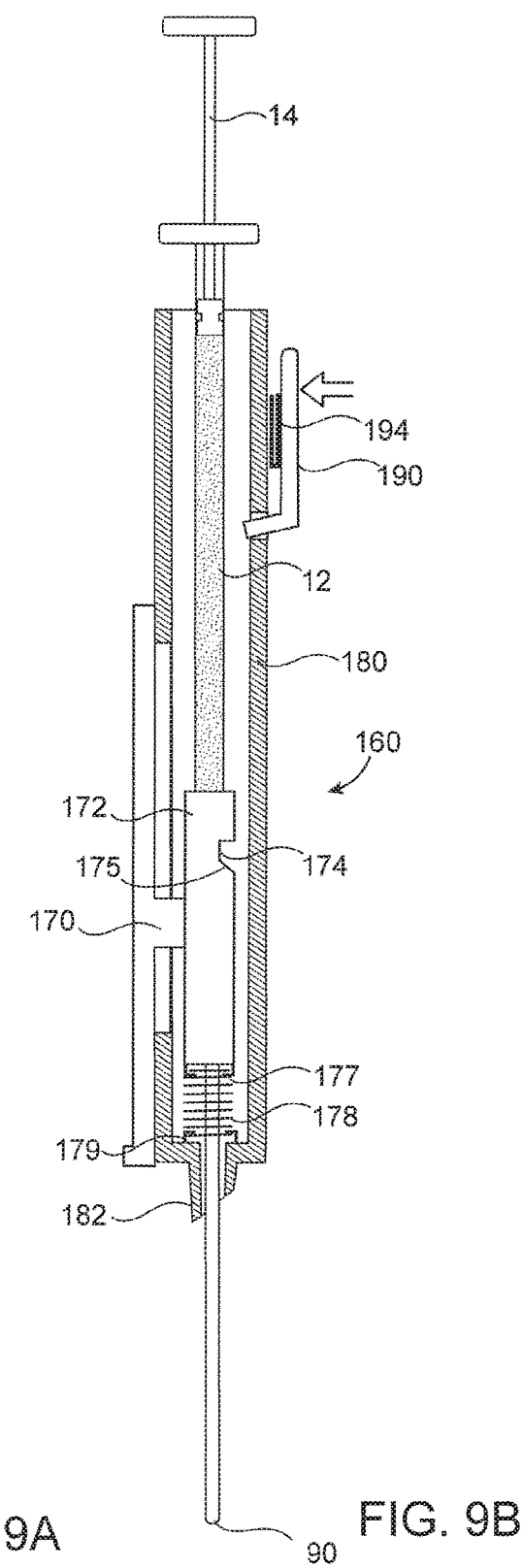
FIG. 9B is a cross-section view of the pull spring transporter assembly embodiment of FIG. 9A after release of the pull spring.

The pull spring integrated needle/cannula 160 embodiment shown in FIGS. 9A-B is similar to the transporter assembly embodiment shown in FIGS. 3-6E except for the addition of a pull spring 178 and a trigger 190. Like the transporter assembly embodiments shown in FIGS. 3-6E, the pull spring integrated cannula 160 shown in FIGS. 9A-B includes a syringe 12 attached to an external transporter housing 170 and a cannula 90. Through connector 172, the external transporter housing 170 is slidably attached to a retractable inner needle tube 180 having a hypodermic needle 182 at its distal end. Between the distal end of the external transporter housing connector 172 and the distal end of the hollow portion of the inner needle tube 180, a pull spring 178 is inserted to connect the two surfaces. Clips 177, 179 are preferably used to attach the ends of the pull spring 178 to the two surfaces. The spring 178 is referred to as a "pull spring" because it is elongated when originally loaded into the integrated/needle cannula 160 (FIG. 9A) and, when released, it compresses to pull the two surfaces together. A trigger 190 is preferably used to hold the pull spring 178 in elongated position until it is ready to be released. In one preferred embodiment, the trigger 190 takes the form of a spring loaded lever 192 that is biased into a notch 174 etched into the external transporter housing connector 172. In this embodiment, the lever 192 is biased with a metallic V-spring 194. Those of skill in the art will recognize that other types of triggers or switches may alternatively be used to hold the pull spring 178 in elongated position until it is ready to be released.

In operation, the pull spring integrated needle/cannula 160 starts with the inner needle tube 180 in its fully forward position so that its hypodermic needle 182 covers and protrudes past the distal end of the cannula 90 (FIG. 9A). The pull spring 178 is held in its elongated position by trigger 190. From this configuration, the medical practitioner inserts the hypodermic needle 182 into the patient's skin. After the hypodermic needle 182 has been inserted, the medical practitioner can push down on trigger 190 while holding onto the external transporter housing 170. As the trigger 190 is pushed down, it is removed from notch 174. This allows the spring 178 to pull the inner needle tube 180 backward so that the hypodermic needle 182 is removed from the patient's skin and transported to its fully retracted position as shown in FIG. 9B. To insure that the cannula 90 remains in the patient as the hypodermic needle 182 is retracted, the distal tip of the cannula should extend nearly to the tip of the hypodermic needle 182 when the hypodermic needle 182 is inserted into the patient's skin (see, FIG. 9A). With the hypodermic needle 182 held in a fully retracted position by pull spring 178 as shown in FIG. 9B, the medical practitioner can maneuver the cannula 90 under the patient's skin to inject sub-dermal substances.

In some instances, the medical practitioner will want to make injections at multiple locations on the patient using the same syringe 12. The pull spring integrated needle/cannula 160 is configured to allow such repeated use. After injection at the first location, the medical practitioner simply pushes the retractable inner needle tube 180 forward relative to the external transporter housing 170 while holding the trigger 190 down until the trigger 190 clicks back into the connector notch 174. When this happens, the pull spring 178 elongates so that the pull spring integrated needle/cannula 160 resumes its original position as shown in FIG. 9A and is ready for re-use. To facilitate re-setting the pull spring integrated needle/cannula 160 in this manner, a ramp 175 is preferably formed at the distal end of the connector notch 176 to guide the trigger 190 into the notch 174.

Figure 10A:
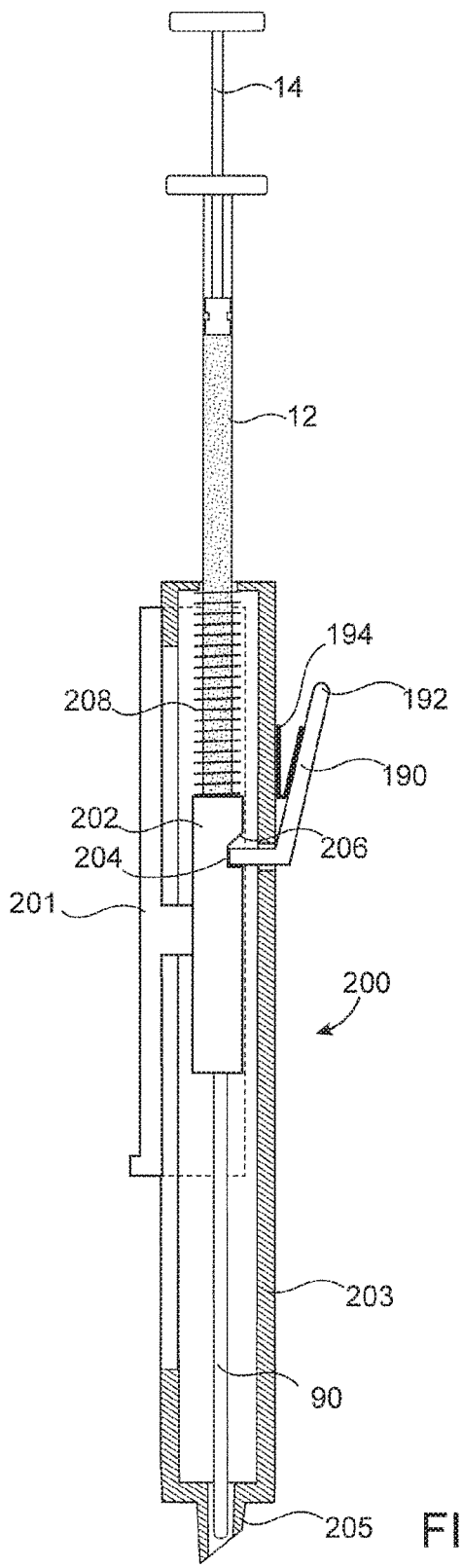
FIG. 10A is a cross-section view of a push spring transporter assembly embodiment prior to release of the push spring.
Figure 10B:
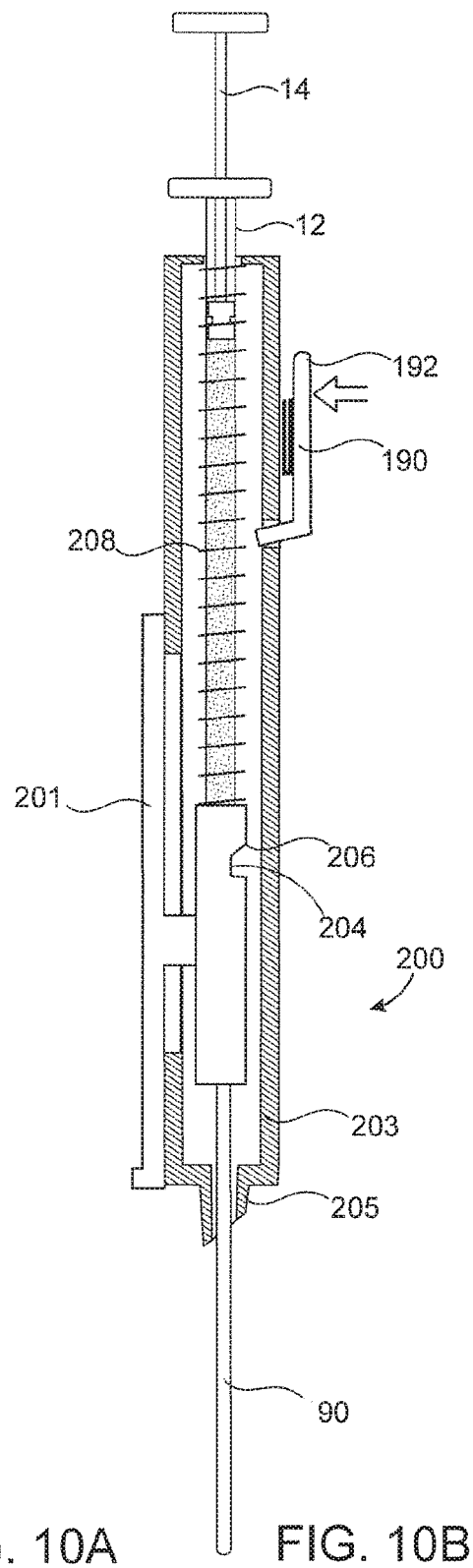
FIG. 10B is a cross-section view of the push spring transporter assembly embodiment of FIG. 10A after release of the push spring.

FIGS. 10A-B show a push spring integrated needle/cannula 200 embodiment that is again similar to the transporter assembly embodiments shown in FIGS. 3-6E and FIGS. 9A-B. Like the transporter assembly embodiments shown in FIGS. 3-6E and 9A-B, the push spring integrated needle/cannula 200 shown in FIGS. 10A-B includes a syringe 12 attached to an external transporter housing 201 and a cannula 90. Through connector 202, the external transporter housing 200 is slidably attached to a retractable inner needle tube 203 having a hypodermic needle 205 at its distal end.

The push spring integrated needle/cannula 200 embodiment shown in FIGS. 10A-B differs from the pull spring integrated needle/cannula 160 embodiment shown in FIGS. 9A-B because the spring 208 is used to push the inner needle tube 203 into a retracted position rather than pull it. In this embodiment, the push spring 208 is located between the proximal end of the external transporter housing connector 202 and the proximal end of the hollow portion of the inner needle tube 203. Again, clips (not shown) are preferably used to attach the ends of the push spring 208 to the two surfaces but are less important here than in the pull spring embodiment because the spring 208 pushes rather than pulls. The spring 208 is referred to as a "push spring" because it is contracted when originally loaded into the integrated needle/cannula 200 (FIG. 10A) and, when released, it expands to push the two surfaces apart. As in the pull spring embodiment, a trigger 190 is preferably used to hold the push spring 208 in a compressed position until it is ready to be released. As before, the trigger 190 can take the form of a spring loaded lever 192 that is biased into a notch 204 etched into the external transporter housing connector 202. Other types of triggers or switches may alternatively be used to hold the push spring 208 in compressed position until it is ready to be released.

In operation, the push spring integrated needle/cannula 200 starts with the inner needle tube 203 in its fully forward position so that its hypodermic needle 205 covers and protrudes slightly past the distal end of the cannula 90 as shown in FIG. 10A. The push spring 208 is held in its compressed position by trigger 190. From this configuration, the medical practitioner inserts the hypodermic needle 205 into the patient's skin. After insertion, the medical practitioner can push down on trigger 190 while holding onto the external transporter housing 201 to expand the spring 208. Referring back to FIG. 3, the medical practitioner can hold the external transporter housing 201 by finger grips 82. In this configuration, the trigger 190 is preferably placed on the upper surface of the inner needle tube 203 between the two finger grips 82. As the trigger 190 is pushed down, it is removed from notch 204. This allows the spring 208 to push the inner needle tube 203 backward so that the hypodermic needle 205 is removed from the patient's skin and transported to its fully retracted position as shown in FIG. 10B. To insure that the cannula 90 remains in the patient as the hypodermic needle 205 is retracted, the distal tip of the cannula 90 should again extend nearly to the tip of the hypodermic needle 205 when the hypodermic needle 205 is inserted into the patient's skin (see, FIG. 10A). With the hypodermic needle 205 held in a fully retracted position by push spring 208 as shown in FIG. 10B, the medical practitioner can maneuver the cannula 90 under the patient's skin to inject sub-dermal substances. The push spring loaded integrated needle/cannula 200 can be reset for use at another patient location by pushing the retractable inner needle tube 203 forward while holding the trigger 190 down until the trigger 190 clicks back into the connector notch 204. A ramp 206 is preferably formed in the connector notch 204 to guide the trigger 190 into the notch 204.

Figure 11G:
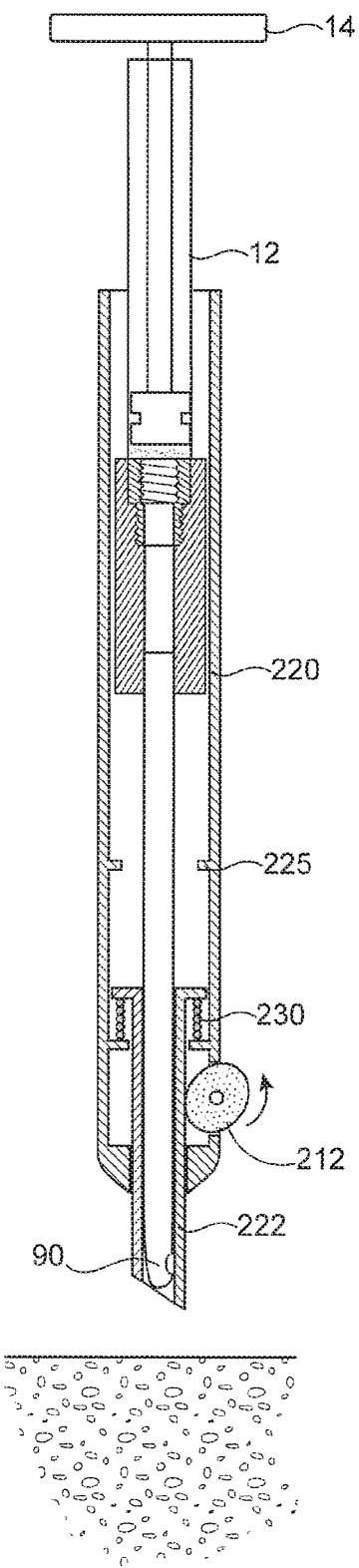
FIG. 11G is a cross-section view of the alternative push spring transporter assembly embodiment of FIG. 11A after is has been reset for repeat use.

FIGS. 11A-G illustrates an alternative push spring integrated needle/cannula 210 embodiment. As illustrated in FIGS. 11A-D, the alternative embodiment 210 has a syringe 12 connected to a cannula 90, preferably through a Luer Lock™ connector in a manner similar to the FIG. 1 embodiment. Attached to the outside of the syringe 12 is a sleeve 221 that can slidably move up and down within an exterior tube 220. At its distal end, the exterior tube 220 has a hypodermic needle 222. Unlike previous embodiments, the hypodermic needle 222 in this embodiment is movable with respect to the exterior tube 220 to which it is attached. As shown in FIGS. 11C-D, a push spring 230 can move the hypodermic needle 222 between the extended position shown in FIG. 11C to the retracted position shown in FIG. 11D. In the FIG. 11C position, a roller switch 212 holds the hypodermic needle 222 in the fully extended position by keeping the push spring 230 contracted. The roller switch 222 is preferably in the shape of an oval to act as a cam and is preferably made from a flexible polymer. When the roller switch 212 is turned as shown in FIG. 11D, the push spring 230 expands to push the hypodermic needle 222 upward until the upper flange 226 of the hypodermic needle 222 presses against exterior tube stop 225. As those of skill in the art will recognize, alternative switches can be used in place of the roller switch 212 shown.

In operation, the alternative push spring integrated needle/cannula 210 starts with the hypodermic needle 222 in the fully extended position shown in FIGS. 11A and 11C. The distal tip of the cannula 90 should be slightly behind the distal tip of the hypodermic needle 222 as shown in FIG. 11C. From this starting configuration, the medical practitioner inserts the hypodermic needle 222 into the patient's skin (FIG. 11C). The medical practitioner then turns the roller switch 212 to release the push spring 230 and retract the hypodermic needle 222 (FIG. 11D). In this retracted position, the hypodermic needle 222 is fully encased in the exterior tube 220 so that it will no longer come in contact with the patient's skin. As the hypodermic needle 222 retracts, it leaves the distal end of the cannula 90 in the patient's skin (FIG. 11D). As shown in FIGS. 11E-F, the syringe 12 and sleeve 221 can then be pushed downward within the exterior tube 220 to advance the cannula 90 deeper into the patient's skin. When the cannula reaches in appropriate position under the patient's skin, the medical practitioner can press down on the plunger 14 to insert sub-dermal substances 91 into the patient (FIG. 11F). If the medical practitioner wants to make multiple injections at different locations in the patient's skin, the roller switch 212 can be turned further as shown in FIG. 11G to re-compress the spring 230 and, in the process, re-extend the hypodermic needle 222 so that the push spring integrated needle/cannula 210 is ready for re-use.

As illustrated in FIGS. 12A-14B, the integrated needle/cannula concepts of the present invention have applications beyond insertion of sub-dermal substances. Absorbable (i.e., dissolvable) or non-absorbable surgical thread can be inserted on the cannula so the cannula acts like a sewing needle. After the hypodermic needle punctures a hole in the patient's skin, the cannula can be used, for example, to push and pull surgical thread through portions of a patent's face to perform a face lift. In the art, this is referred to as a "thread-lift." Suitable surgical threads include, but are not limited to, gold thread as well as Mono/Screw/Tornado/CogV forms of polydioxanone (PDO) thread. To aid insertion, the surgical thread can be barbed or include multiple spherical bumps. As will be recognized by this of skill in the art, all the previously described embodiments can be modified to perform thread-lift procedures.

Figure 12A:
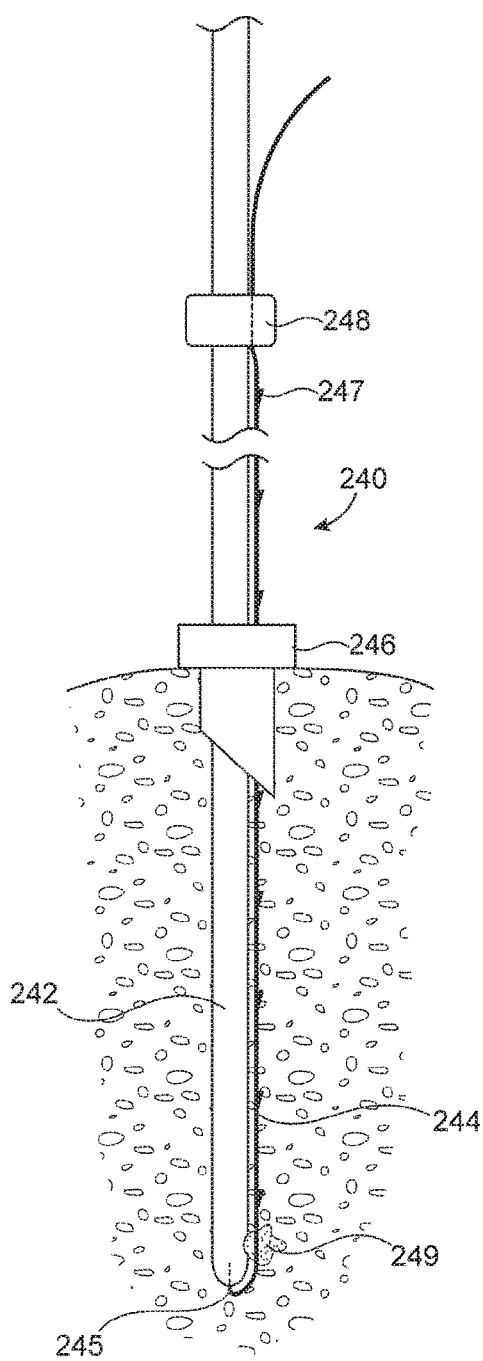
FIG. 12A illustrates a cut-away view of an integrated needle and cannula that includes an exterior surgical thread for a thread-lift procedure.
Figure 12B:
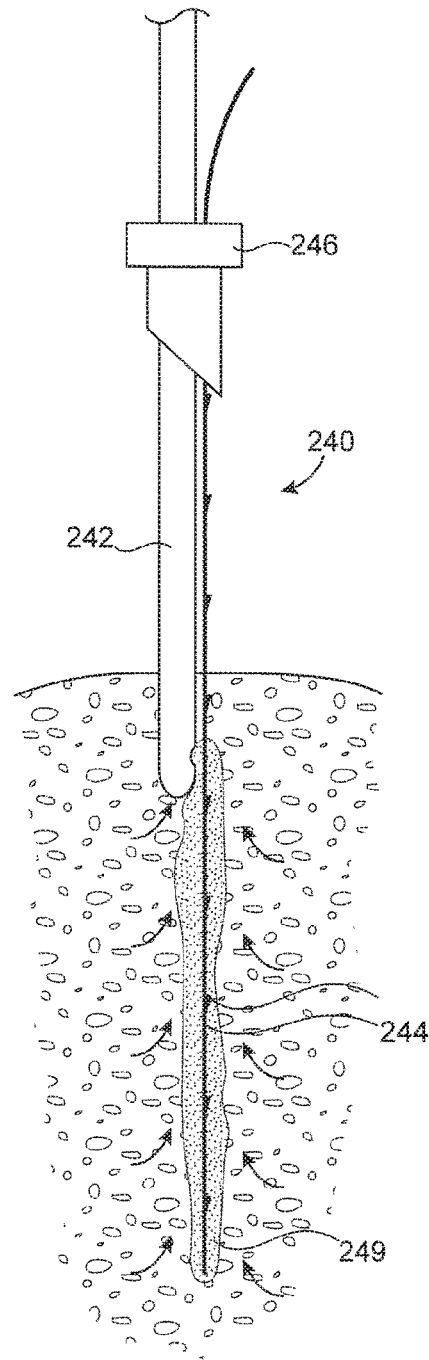
FIG. 12B illustrates the threaded needle/cannula embodiment of FIG. 12A after the thread has been inserted into a patient's skin.

FIG. 12A illustrates an integrated needle and cannula 240 of the present invention similar to the FIG. 1 integrated needle and cannula embodiment except for the addition of an exterior surgical thread 244. Like the FIG. 1 embodiment, this integrated needle and cannula embodiment 240 includes a hypodermic needle device 246 and a concentric cannula 242. The surgical thread 244 is preferably attached to the distal end 245 of the cannula 242 and then threaded through the concentric space between the cannula 242 and hypodermic needle device 246. A foam ring 248 may be placed around the thread 244 and cannula 242 to keep the thread 244 adjacent to the cannula 242. The surgical thread 244 may have barbs 247 to hook into the patient's skin as the cannula 242 is being retracted. FIG. 12A illustrates the integrated needle and cannula 240 after the hypodermic needle device 246 has punctured the patient's skin and the cannula 242 has been introduced. FIG. 12B illustrates subsequent retraction of the hypodermic needle device 246 to allow free sub-dermal movement of the cannula 242. In this FIG. 12B, the cannula 242 is in the process of being withdrawn to leave the surgical thread 244 behind. For better results, filler 249 may also be deposited by a syringe (see FIG. 1) at the same time the surgical thread 244 is being inserted.

Figure 13A:
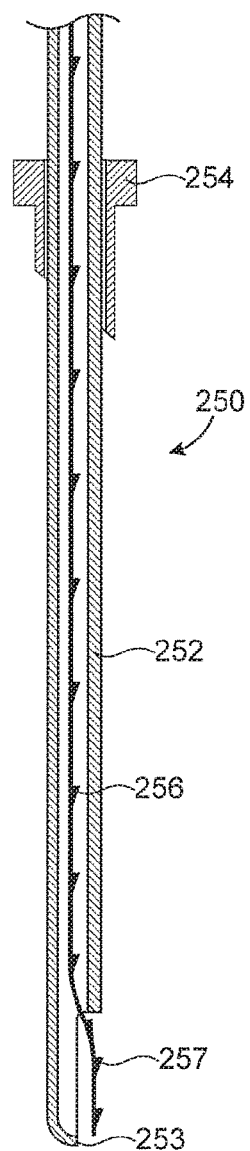
FIG. 13A illustrates a cut-away view of an integrated needle and cannula that includes an interior surgical thread for a thread-lift procedure.
Figure 13B:
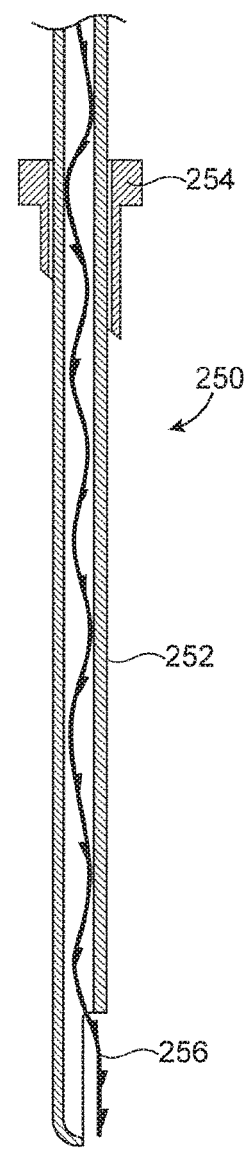
FIG. 13B illustrates the threaded needle/cannula embodiment of FIG. 13A where the interior surgical thread is more coiled.

FIGS. 13A and 13B illustrates another integrated needle and cannula embodiment 250 that is useful for thread-lift procedures. Like the FIG. 12A embodiment, this integrated needle and cannula embodiment 250 includes a hypodermic needle device 254, a concentric cannula 252 and a surgical thread 256 with barbs 257. Nonetheless, this integrated needle and cannula embodiment 250 differs from the FIG. 12A embodiment insofar as the surgical thread 256 is inside, rather than outside of, the cannula 252 and the cannula tip 253 is partially open. Having the thread 256 inside the cannula 252 can make the thread 256 easier to control. FIG. 13B illustrates how the surgical thread 256 in the FIG. 13A embodiment can be coiled to allow more of it to be stored in the cannula 252.

Figure 14A:
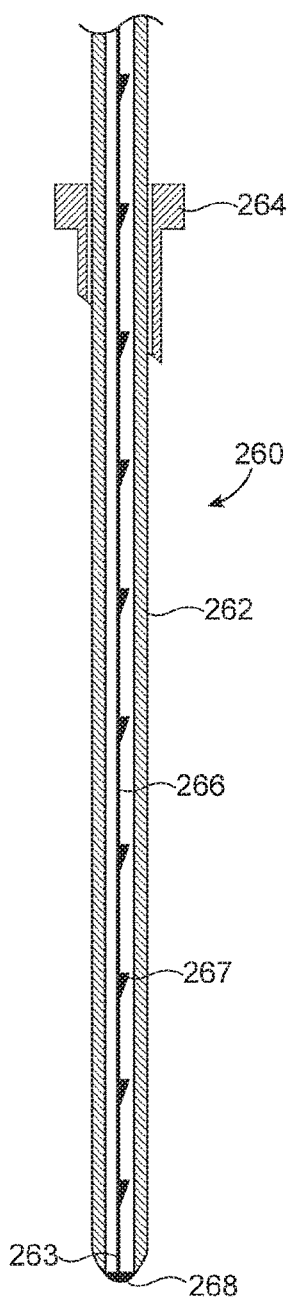
FIG. 14A illustrates a cut-away view of an integrated needle and cannula with an interior surgical thread where the cannula is open ended.
Figure 14B:
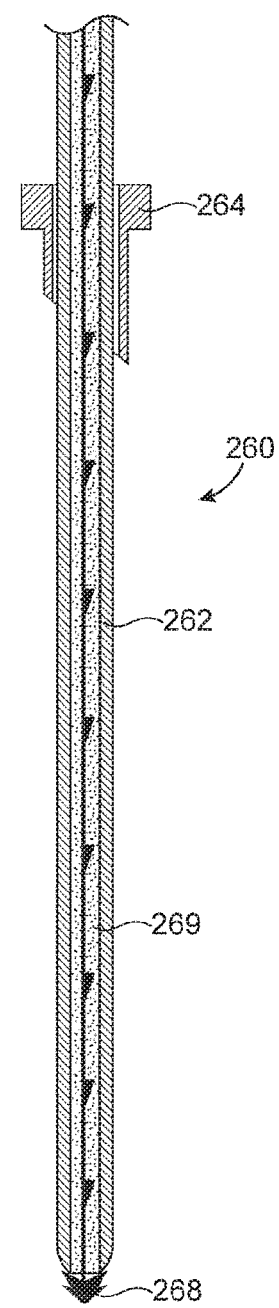
FIG. 14B illustrates the threaded needle/cannula embodiment of FIG. 14A where filler is injected at the same time as surgical thread.

FIGS. 14A and 14B illustrates a further integrated needle and cannula embodiment 260 having an interior surgical thread 266 for thread-lift procedures. Like the FIG. 13A embodiment, it has a concentric cannula 262, a hypodermic needle device 264 and an interior surgical thread with barbs 267. The FIGS. 14A and 14B embodiment differs from the FIG. 13A embodiment insofar as the distal end 263 of the cannula 262 is fully open. This allows the distal end 268 of the surgical thread 266 to feed directly out of the cannula end 263. FIG. 14B illustrates that a syringe (FIG. 1) can be used to pass filler through the distal end 263 of the cannula 262 while the barbed surgical thread 266 is being placed under the patient's skin.

In the foregoing specification, the invention has been described with reference to specific preferred embodiments and methods. It will, however, be evident to those of skill in the art that various modifications and changes may be made without departing from the broader spirit and scope of the invention as set forth in the appended claims. For these reasons, the specification and drawings are, accordingly, to be regarded in an illustrative, rather than restrictive sense; the invention being limited only by the appended claims.

What is claimed is:

1. An integrated needle and cannula assembly comprising:
    a syringe;
    a transporter assembly having an external transporter housing and an inner needle tube slidably and concentrically located within a hollow annular space of said external transporter housing;
    wherein said external transporter housing is attached at opposite ends to a syringe and to a cannula;
    further wherein said inner needle tube is attached to the proximal end of a hypodermic needle having a hollow annular space such that said cannula is inserted concentrically into the hollow annular space of said hypodermic needle and said cannula is at least twice as long as said hypodermic needle.

2. The integrated needle and cannula assembly of claim 1 wherein said external transporter housing has a connector which connects said external transporter housing to said syringe and said cannula.

3. The integrated needle and cannula assembly of claim 2 wherein said connector is concentrically located within a hollow annular space of said inner needle tube.

4. The integrated needle and cannula assembly of claim 3 wherein said connector has a base attaching said connector to said external transporter housing.

5. The integrated needle and cannula assembly of claim 4 wherein said inner needle tube has an annular gap which fits around said connector base.

6. The integrated needle and cannula assembly of claim 1 wherein said cannula is a blunt-tipped cannula.

7. The integrated needle and cannula assembly of claim 6 wherein said blunt-tipped cannula is approximately 1.5 inches in length and 27 gauge.

8. The integrated needle and cannula assembly of claim 1 wherein said external transporter housing and inner needle tube are generally cylindrical in shape.

9. The integrated needle and cannula assembly of claim 1 further comprising a spring capable of slidably retracting said inner needle tube relative to said external transporter housing.

10. The integrated needle and cannula assembly of claim 9 wherein said spring pulls said inner needle tube to retract said inner needle tube relative to said external transporter housing.

11. The integrated needle and cannula assembly of claim 9 wherein said spring pushes said inner needle tube to retract said inner needle tube relative to said external transporter housing.

12. The integrated needle and cannula assembly of claim 9 further comprising a trigger to activate spring movement.

13. The integrated needle and cannula assembly of claim 12 wherein said trigger is spring biased.

14. An integrated needle and cannula assembly for injection of medical substances underneath animal dermal tissue comprising:
    a syringe;
    a transporter assembly having an external transporter housing and an inner needle tube slidably and concentrically located within a hollow annular space of said external transporter housing;
    said external transporter housing is attached at opposite ends to a syringe and to a cannula;
    said inner needle tube is attached to the proximal end of a hypodermic needle having a hollow annular space such that said cannula is inserted concentrically into the hollow annular space of said hypodermic needle; and,
    wherein said hypodermic needle can puncture said dermal tissue and retract relative to said cannula so that said medical substances are sub-dermally injected through said cannula without said hypodermic needle touching dermal tissue during injection.

15. The integrated needle and cannula assembly of claim 14 further comprising a spring capable of retracting said hypodermic needle relative to said cannula.

16. The integrated needle and cannula assembly of claim 15 further comprising a trigger to activate spring movement.

17. The integrated needle and cannula assembly of claim 14 wherein said cannula is a blunt-tipped cannula.

* * * * *